United States Patent
Ramasamy et al.

(10) Patent No.: US 11,139,501 B2
(45) Date of Patent: Oct. 5, 2021

(54) ENGINEERED PHOTOSYNTHETIC ORGANISMS, PHOTOSYNTHETIC ELECTRODES INCLUDING THE ENGINEERED PHOTOSYNTHETIC ORGANISMS, PHOTOSYNTHETIC BIOELECTROCHEMICAL CELLS AND PHOTOSYNTHETIC FUEL CELLS

(71) Applicant: University of Georgia Research Foundation, Inc., Athens, GA (US)

(72) Inventors: Ramaraja P. Ramasamy, Watkinsville, GA (US); Narendran Sekar, Malden, MA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/918,066

(22) Filed: Jul. 1, 2020

(65) Prior Publication Data

US 2020/0335809 A1 Oct. 22, 2020

Related U.S. Application Data

(62) Division of application No. 15/576,136, filed as application No. PCT/US2016/032868 on May 17, 2016, now Pat. No. 10,741,863.

(60) Provisional application No. 62/164,821, filed on May 21, 2015.

(51) Int. Cl.
| | |
|---|---|
| *C12N 15/74* | (2006.01) |
| *H01M 8/16* | (2006.01) |
| *H01M 14/00* | (2006.01) |
| *C07K 19/00* | (2006.01) |
| *C12N 9/02* | (2006.01) |
| *C12P 3/00* | (2006.01) |

(52) U.S. Cl.
CPC .............. *H01M 8/16* (2013.01); *C07K 19/00* (2013.01); *C12N 9/0004* (2013.01); *C12N 9/0071* (2013.01); *C12N 9/0095* (2013.01); *C12N 15/74* (2013.01); *C12P 3/00* (2013.01); *H01M 14/00* (2013.01); *Y02E 60/50* (2013.01); *Y02P 20/133* (2015.11)

(58) Field of Classification Search
CPC ......... C12N 15/74; C12N 9/0071; C12P 3/00; C07K 19/00
See application file for complete search history.

(56) References Cited

PUBLICATIONS

J. M. Pisciotta, Y. Zou and I. V. Baskakov, Plos One, 2010, 5.
N. Sekar, Y. Umasankar and R. P. Ramasamy, Physical Chemistry Chemical Physics, 2014, 16, 7862-7871.
B. E. Logan, Nature Reviews Microbiology, 2009, 7, 375-381.
Y. Yang, M. Xu, J. Guo and G. Sun, Process Biochemistry, 2012, 47, 1707-1714.
D. R. Lovley, Current Opinion in Biotechnology, 2008, 19, 564-571.
T. Mehta, M. V. Coppi, S. E. Childers and D. R. Lovley, Applied and Environmental Microbiology, 2005, 71, 8634-8641.
X. Qian, T. Mester, L. Morgado, T. Arakawa, M. L. Sharma, K. Inoue, C. Joseph, C. A. Salgueiro, M. J. Maroney and D. R. Lovley, Biochimica Et Biophysica Acta-Bioenergetics, 2011, 1807, 404-412.
C. Leang, X. Qian, T. Mester and D. R. Lovley, Applied and Environmental Microbiology, 2010, 76, 4080-4084.
R. E. Blankenship, D. M. Tiede, J. Barber, G. W. Brudvig, G. Fleming, M. Ghirardi, M. R. Gunner, W. Junge, D. M. Kramer, A. Melis, T. A. Moore, C. C. Moser, D. G. Nocera, A. J. Nozik, D. R. Ort, W. W. Parson, R. C. Prince and R. T. Sayre, Science, 2011, 332, 805-809.
N. B. Ivleva, M. R. Bramlett, P. A. Lindahl and S. S. Golden, Embo Journal, 2005, 24, 1202-1210.
Leang, C., et al. (2003). "OmcB, a c-type polyheme cytochrome, involved in Fe(III) reduction in Geobacter sulfurreducens." Journal of Bacteriology 185(7): 2096-2103.
R. W. Bradley, P. Bombelli, D. J. Lea-Smith and C. J. Howe, Physical Chemistry Chemical Physics, 2013, 15, 13611-13618.
N. Sekar, R. Jain, Y. Yan and R. P. Ramasamy, Biotechnology Bioengineering, 2016, 113(3): 675-679.
Inoue, K., et al. (2010). "Purification and Characterization of OmcZ, an Outer-Surface, Octaheme c-Type Cytochrome Essential for Optimal Current Production by Geobacter sulfurreducens." Applied and Environmental Microbiology 76(12): 3999-4007.
S. Tsujimura, A. Wadano, K. Kano and T. Ikeda, Enzyme and Microbial Technology, 2001, 29, 225-231.
J. E. Butler, F. Kaufmann, M. V. Coppi, C. Nunez and D. R. Lovley, Journal of Bacteriology, 2004, 186, 4042-4045.
J. R. Lloyd, C. Leang, A. L. H. Myerson, M. V. Coppi, S. Cuifo, B. Methe, S. J. Sandler and D. R. Lovley, Biochemical Journal, 2003, 369, 153-161.
J. L. Cape, M. K. Bowman and D. M. Kramer, Trends in Plant Science, 2006, 11, 46-55.
C. Obinger, J. C. Knepper, U. Zimmermann and G. A. Peschek, Biochemical and Biophysical Research Communications, 1990, 169, 492-501.

(Continued)

*Primary Examiner* — Tekchand Saidha

(74) *Attorney, Agent, or Firm* — Thomas Horstemeyer, LLP

(57) ABSTRACT

The present disclosure provides engineered photosynthetic cells and organisms, methods for engineering photosynthetic cells and organisms with increased extracellular electron transport, photo-bioelectrochemical cells (PBECs), anodes for a PBECs and/or photosynthetic microbial fuel cells (PMFCs), methods of generating an electrical current with PBECs, and methods and systems for generating $H_2$ fuel.

19 Claims, 13 Drawing Sheets

Specification includes a Sequence Listing.

(56) References Cited

PUBLICATIONS

W. F. J. Vermaas, Photosynthesis and Respiration in Cyanobacteria, Macmillan Publishers Ltd, Nature Publishing Group, 2001.
J. M. Pisciotta, Y. Zou and I. V. Baskakov, Applied Microbiology and Biotechnology, 2011, 91, 377-385.
Baron, D., et al. (2009). "Electrochemical Measurement of Electron Transfer Kinetics by Shewanella oneidensis MR-1." Journal of Biological Chemistry 284(42): 28865-28873.
Carmona-Martinez, A. A., et al. (2013). "Electron transfer and biofilm formation of Shewanella putrefaciens as function of anode potential." Bioelectrochemistry 93: 23-29.

ENGINEERED PHOTOSYNTHETIC ORGANISMS, PHOTOSYNTHETIC ELECTRODES INCLUDING THE ENGINEERED PHOTOSYNTHETIC ORGANISMS, PHOTOSYNTHETIC BIOELECTROCHEMICAL CELLS AND PHOTOSYNTHETIC FUEL CELLS

CROSS-REFERENCE TO RELATED APPLICATIONS

This application is a Divisional of U.S. application Ser. No. 15/576,136 filed on Nov. 21, 2017, which is the 35 U.S.C. § 371 national stage of PCT application having serial number PCT/US2016/032868, filed on May 17, 2016, which application also claims priority to U.S. provisional application entitled "ENGINEERED PHOTOSYNTHETIC ORGANISMS, PHOTOSYNTHETIC ELECTRODES INCLUDING THE ENGINEERED PHOTOSYNTHETIC ORGANISMS, PHOTOSYNTHETIC BIOELECTROCHEMICAL CELLS AND PHOTOSYNTHETIC FUEL CELLS," having Ser. No. 62/164,821 filed on May 21, 2015, each of which is entirely incorporated herein by reference.

SEQUENCE LISTING

This application contains a sequence listing filed in electronic form as an ASCII.txt file entitled 222102-2710_25.txt, created on May 17, 2016 and having a size of 7 KB. The content of the sequence listing is incorporated herein in its entirety.

BACKGROUND

Generating clean power from renewable sources to meet all or most of world's energy needs is a goal that will not occur without a transformational change in energy harvesting methods. Among the available options, solar energy stands out as a ubiquitous renewable source. The solar (light) energy is converted into useful chemical energy (food) by photosynthesis, a process that evolved over 2.5 billion years. Mimicking or engineering this biological phenomenon could provide a renewable alternative energy technology that is nature-inspired, clean, environment friendly and self-sustainable.

Plant photosynthesis provides an unmatched quantum efficiency of nearly 100%. In recent years, significant interest has evolved in mimicking and/or harnessing the photosynthetic process for energy conversion and hydrogen generation applications. Multiple approaches to artificial photosynthesis exist, including light energy harvesting using natural pigments from plants and microorganisms and using whole cell microorganisms. Scientists have explored photosynthetic organelles such as thylakoids, chlorophyll molecules, photosystems, and oxygen evolving complexes for photo-electrochemical activity. However, isolated organelles tend to lack the stability of whole cells or organisms.

Microorganisms capable of transferring electrons to extracellular electron acceptors as a part of their metabolism are called exoelectrogens. The extracellular electron transfer (EET) capability of microorganisms has been exploited in microbial fuel cells (MFC) to generate electricity using organics as fuel. When deprived of their cellular terminal electron acceptor, these microorganisms prefer to dump their electrons to the electrode, thereby using it as an alternate electron sink. In MFC, the commonly used exoelectrogens such as *Geobacter* sp. and *Shewanella* sp. consume organic carbon sources such as acetate or lactate as their reductant and transfer the electrons from their respiratory electron transport chain to the anode while simultaneously releasing $CO_2$. On the contrary, photosynthesis based electricity generation using cyanobacteria requires only light and water without the need of any external organic carbon source and therefore offers huge potential for development of a clean, renewable and environmentally friendly alternate energy source. Cyanobacteria have inherent ability to perform EET and are shown to generate electricity in photo-bioelectrochemical fuel cells. However, the current densities of photo bio-electrochemical cells (PBECs) and/or photosynthetic microbial fuel cells (PMFCs) based on photosynthetic microorganisms such as cyanobacteria generate current densities lower than that of standard solar cells, and the power density achieved using cyanobacteria is roughly two orders of magnitude lower compared to that produced by the exoelectrogens in MFC. Thus, cyanobacteria based PBECs and PMFCs are currently not competitive against biofuel cell and photovoltaic technologies or standard solar cells.

SUMMARY

The present disclosure provides engineered photosynthetic cells and/or organisms with increased extracellular electron transport, methods for producing engineered photosynthetic cells and/or organisms, methods for producing engineered photosynthetic cyanobacteria with increased extracellular electron transport, anodes for a photo-bioelectrochemical cell or a photosynthetic microbial fuel cell, photo-bioelectrochemical cells (PBEC), photosynthetic microbial fuel cells (PMFC), and methods of generating an electrical current and/or $H_2$ fuel using the PBECs and/or PMFCs of the present disclosure.

In embodiments, the present disclosure provides engineered photosynthetic cells and/or organisms including an exogenous nucleic acid molecule encoding a non-native redox enzyme capable of extracellular electron transport and a promoter operatively linked to the nucleic acid molecule encoding the redox enzyme. The redox non-native enzyme is expressed in the cell or organism into which it is transformed, such that the engineered photosynthetic cell or organism has increased extracellular electron transport compared to a corresponding wild-type cell or organism. In embodiments, the engineered photosynthetic organism is a cyanobacterium. In embodiments, the non-native redox enzyme is an electro active terminal reductase from an exoelectrogenic organism.

Method of the present disclosure for producing an engineered photosynthetic cyanobacteria with increased extracellular electron transport, in embodiments, include: providing a cyanobacterium; transforming the cyanobacterium with an expression vector including an expression cassette including a nucleic acid molecule encoding an outer membrane cytochrome (Omc) from *Geobacter*, a promoter operatively linked to the nucleic acid encoding the Omc, and a nucleic acid encoding a selective marker operatively linked to the nucleic acid encoding the Omc, and a targeting sequence directing insertion of the expression cassette into the cyanobacteria genome; and selecting for transformed cyanobacterium expressing the Omc.

Embodiments of anodes for PBECs or PMFCs of the present disclosure include: an anode material, one or more engineered photosynthetic cells or organisms of the present disclosure, and a nanostructured material in electrochemical communication with the engineered photosynthetic organism or cell. The one or more engineered photosynthetic cells or organisms on the anode include an exogenous nucleic acid molecule encoding a non-native redox enzyme capable of extracellular electron transport, where the redox enzyme is expressed in the engineered photosynthetic organism or cell, and where the engineered photosynthetic cell or organism has increased extracellular electron transport compared to a corresponding wild-type cell or organism. The engineered photosynthetic organism or cell is capable of oxidizing water molecules and generating electrons using a light induced photo-electrochemical reaction where at least a portion of electrons generated by the photosynthetic organism or cell are transferred to the anode material via direct electron transfer.

PBECs of the present disclosure include, in embodiments, an anode of the present disclosure and a cathode composite including a cathode and at least one enzyme or metallic catalyst capable of reducing $O_2$.

Embodiments of methods of the present disclosure for generating electrical current include providing a PBEC including an anode of the present disclosure and a cathode composite including a cathode and at least one enzyme or metallic catalyst capable of reducing $O_2$, and exposing the PBEC to light in the presence of water, where the engineered photosynthetic cell(s) or organism(s) uses light energy to oxidize a water molecule and generate electrons, which are transferred to the anode via the nanostructured material, and where electrons generated at the anode reduce $O_2$ at the cathode, thereby inducing a potential difference between the anode and the cathode and generating an electrical current.

Embodiments of PMFCs of the present disclosure include an anode of the present disclosure and a cathode composite including a cathode capable of reducing $H^+$ to produce $H_2$.

Embodiments of methods of the present disclosure for generating $H_2$ fuel include providing a PMFC including an anode of the present disclosure and a cathode composite including a cathode capable of reducing $H^+$ to produce $H_2$, and exposing the PMFC to light in the presence of water, where the engineered photosynthetic cell(s) or organism(s) uses light energy to oxidize a water molecule and generate electrons, which are transferred to the anode via the nanostructured material, and where electrons generated at the anode reduce $H^+$ at the cathode, thereby generating $H_2$.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure.

FIG. 3A is a schematic illustrating integration of omcS by homologous recombination, with NSI: neutral site I; Spec®: spectinomycin resistance gene; $P_{trc}$: IPTG inducible trc promoter. FIG. 3B is a digital image confirmation of successful cloning of omcS by PCR. Eng-CB 1/2/3: three different colonies screened and found to be positive; Wild-CB: wild type *S. elongatus*; POS: pNR1 vector positive control.

DETAILED DESCRIPTION

Figure 1:
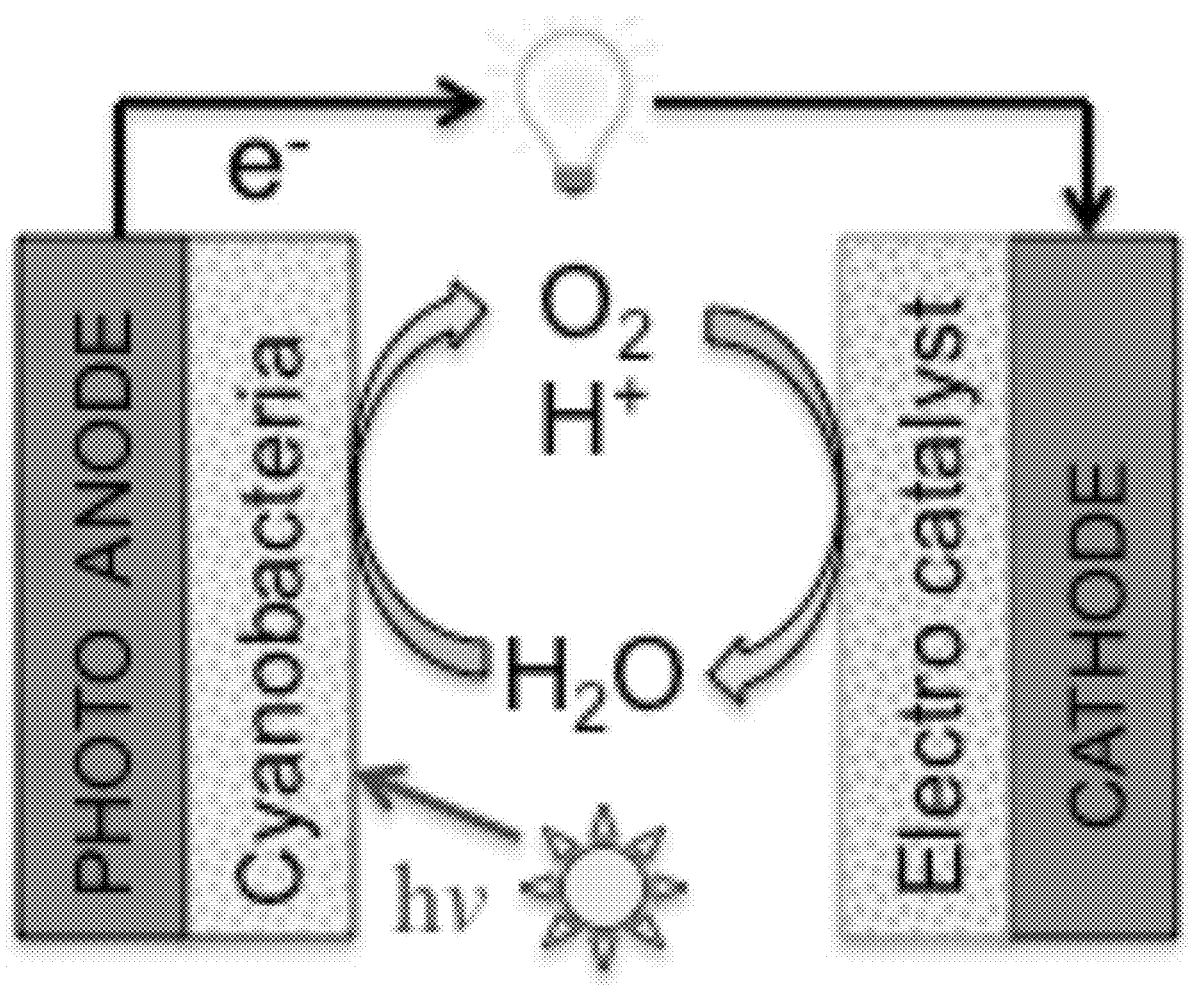
FIG. 1 illustrates a representation of a biological solar cell to generate power from light and water using cyanobacteria.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Of the publications and patents cited in this specification, those that are incorporated by reference are specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, organic chemistry, biochemistry, genetics, botany, nanotechnology, electrochemistry and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps. Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

As used herein, the term "photosynthetic organism" includes an organism, whether single or multi-cellular, capable of carrying out the photosynthetic process of harnessing light energy to induce photochemical oxidation of water molecules to generate electrons. As used herein, the term "photosynthetic cell" includes a single cell, whether a whole single-cellular organism or a single cell of a multi-cellular organism (e.g., isolated from such organism), capable of carrying out the photosynthetic process. Thus, in some instances, a photosynthetic cell is also a photosynthetic organism (e.g., a cyanobacterium).

As used herein, the term "photosynthetic compound" includes any compound involved in the photosynthetic process, e.g., the process of harnessing light energy to induce a photochemical reaction to oxidize water molecules and generate electrons. "Photosynthetic compounds" include "photosynthetic proteins" and protein complexes, such as, but not limited to, PSI, PSII, cyt $b_6f$, plastocyanin, phycocyanin, and phycoerythrin as well as other non-protein, photosynthetic molecules, such as, but not limited to, plastoquinone and carotenoids. The photosynthetic compounds of the present disclosure may be isolated from the host organism and organelles in which they originate, or they may be located in a thylakoid membrane or thylakoid organelle or photosynthetic bacterial organism.

As used herein, the term "photosynthetic reaction center" (PSRC) refers to one or more photosynthetic compounds as defined above. A PSRC may include a single photosynthetic compound (e.g., PSII) or it may contain a group of photosynthetic compounds, whether isolated or working in a cluster or entity (e.g., in a thylakoid membrane, photosynthetic cell, and/or photosynthetic organism). A PSRC, as used in the present disclosure, has the ability to harness light energy to induce a photochemical reaction to oxidize water molecules and generate electrons.

As used herein, the term "extracellular electron transport" or "extracellular electron transfer" (EET) refers to the transfer of electrons outside of the cellular membrane of a photosynthetic cell/organism to an external (e.g., extracellular) electron acceptor. Organisms capable of such extracellular electron transport are called "exoelectrogens".

As used in the present disclosure, two materials are in "electrochemical communication" when electrons generated by a chemical reaction of one material (e.g., photosynthetic reaction centers) can be transferred to and/or accepted by the other material (e.g., nanostructured material and/or electrode).

"Direct electron transfer," as used in the present application, indicates that an electron can be transferred to an electrode (e.g., anode) from a photosynthetic cell/organism that catalyzed the reaction that produced the electron, as opposed to having to be transferred to the electrode by a separate shuttle molecule (e.g., a redox mediator or redox shuttle). In embodiments of the present application, direct electron transfer includes the transfer of electrons generated from a photosynthetic compound/reaction center in the cell/organism to the electrode through a nanostructured material or matrix of nanostructured materials, such as where the nanostructured material couples the photosynthetic organism/cell to the electrode. The presence of direct electron transfer in an electrochemical cell of the present disclosure does not preclude the existence of some electron transfer occurring through a mediator, it just indicates that direct electron transfer is occurring in the cell.

As used herein, the term "anode" or "anode composite" refers to a construct that provides the anode function in a photosynthetic electrochemical cell of the present disclosure. In embodiments, the anode/anode composite includes an anode/anode material as well as any other materials or components coupled to the anode that provide for the oxidizing capability of the anode (e.g., nanostructured matrix material, photosynthetic organism/cell, and the like, as well as compounds or liking agents used to couple the anode to the other components of the anode composite). Similarly, the term "cathode" or "cathode composite" refers to a construct that includes the cathode/cathode material as well as other materials that provide for the reducing activity of the cathode (e.g., the cathode and a compound capable of reducing $O_2$ or producing $H_2$, as well as any compounds or agents used to couple the cathode to the other components of the cathode composite, such as nanostructured materials and/or any linking agents).

The term "matrix of nanostructured materials", as used in the present disclosure, includes a network or multi-dimensional structure of nanoparticles capable of coupling photosynthetic cells/organisms to an electrode.

"Redox mediator" or "redox shuttle" refers to a compound capable of assisting in the transfer of electrons between a redox enzyme (e.g., a photosynthetic compound of the present disclosure that oxidizes water and generates electrons) and an electrode.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein.

A "gene" typically refers to a hereditary unit corresponding to a sequence of DNA that occupies a specific location on a chromosome and that contains the genetic instruction for a characteristic(s) or trait(s) in an organism.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome.

As used herein, "transformation" or "transformed" refers to the introduction of a nucleic acid (e.g., DNA or RNA) into cells in such a way as to allow expression of the coding portions of the introduced nucleic acid.

As used herein a "transformed cell" is a cell transfected with a nucleic acid sequence. As used herein, a "transgene" refers to an artificial nucleic acid which is used to transform a cell of an organism, such as a bacterium or a plant.

As used herein, "transgenic" refers to a cell, tissue, or organism that contains a transgene.

As used herein, the term "exogenous DNA" or "exogenous nucleic acid sequence" or "exogenous polynucleotide" refers to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

As used herein, "isolated" indicates removed or separated from the native environment. Therefore, isolated DNA can contain both coding (exon) and noncoding regions (introns) of a nucleotide sequence corresponding to a particular gene. An isolated peptide or protein indicates the protein is separated from its natural environment. Isolated nucleotide sequences and/or proteins are not necessarily purified. For instance, an isolated nucleotide or peptide may be included in a crude cellular extract or they may be subjected to additional purification and separation steps.

With respect to nucleotides, "isolated nucleic acid" refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example but not limited to, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, e.g., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

It is advantageous for some purposes that a nucleotide sequence or peptide is in purified form. The term "purified" in reference to nucleic acid and/or peptide sequence represents that the sequence has increased purity relative to the natural environment.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide (e.g., a variant of a CCD enzyme) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

The term "expression" as used herein describes the process undergone by a structural gene to produce a polypeptide. It is a combination of transcription and translation. Expression generally refers to the "expression" of a nucleic acid to produce a polypeptide, but it is also generally acceptable to refer to "expression" of a polypeptide, indicating that the polypeptide is being produced via expression of the corresponding nucleic acid.

As used herein, the term "over-expression" and "up-regulation" refers to the expression of a nucleic acid encoding a polypeptide (e.g., a gene) in a transformed plant cell at higher levels (therefore producing an increased amount of the polypeptide encoded by the gene) than the "wild type" plant cell (e.g., a substantially equivalent cell that is not transfected with the gene) under substantially similar conditions. Thus, to over-express or increase expression of an CCD nucleic acid refers to increasing or inducing the production of the CCD polypeptide encoded by the nucleic acid, which may be done by a variety of approaches, such as increasing the number of genes encoding for the polypeptide, increasing the transcription of the gene (such as by placing the gene under the control of a constitutive promoter), or increasing the translation of the gene, or a combination of these and/or other approaches. Conversely, "under-expression" and "down-regulation" refers to expression of a polynucleotide (e.g., a gene) at lower levels (producing a decreased amount of the polypeptide encoded by the polynucleotide) than in a "wild type" plant cell. As with over-expression, under-expression can occur at different points in the expression pathway, such as by decreasing the number of gene copies encoding for the polypeptide, inhibiting (e.g., decreasing or preventing) transcription and/or translation of the gene (e.g., by the use of antisense nucleotides, suppressors, knockouts, antagonists, etc.), or a combination of such approaches.

The term "plasmid" as used herein refers to a non-chromosomal double-stranded DNA sequence including an intact "replicon" such that the plasmid is replicated in a host cell.

As used herein, the term "vector" or "expression vector" is used in reference to a vehicle used to introduce an exogenous nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast DNA, bacterial genomic or plasmid DNA, or viral DNA, or may contain elements of more than one of these.

As used herein, the term "expression system" includes a biologic system (e.g., a cell based system) used to express a polynucleotide to produce a protein. Such systems generally employ a plasmid or vector including the polynucleotide of interest, where the plasmid and/or expression vector is constructed with various elements (e.g., promoters, selectable markers, etc.) to enable expression of the protein product from the polynucleotide. Expression systems use the host system/host cell transcription and translation mechanisms to express the product protein. Common expression systems include, but are not limited to, bacterial expression systems (e.g., *E. coli*), yeast expression systems, viral expression systems, animal expression systems, and plant expression systems.

As used herein, the term "promoter" or "promoter region" includes all sequences capable of driving transcription of a coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

The term "operably linked" indicates that the regulatory sequences for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers in an expression vector.

As used herein, the term "selectable marker" refers to a gene whose expression allows one to identify cells that have been transformed or transfected with a vector containing the marker gene. For instance, a recombinant nucleic acid may include a selectable marker operably linked to a gene of interest and a promoter, such that expression of the selectable marker indicates the successful transformation of the cell with the gene of interest.

The terms "native," "wild type", or "unmodified" in reference to an organism (e.g., plant or cell), polypeptide, protein or enzyme, are used herein to provide a reference point for a variant/mutant of an organism, polypeptide, protein, or enzyme prior to its mutation and/or modification (whether the mutation and/or modification occurred naturally or by human design). Typically, the unmodified, native, or wild type organism, polypeptide, protein, or enzyme has an amino acid sequence that corresponds substantially or completely to the amino acid sequence of the polypeptide, protein, or enzyme as it generally occurs naturally.

An "enzyme," as used herein, is a polypeptide that acts as a catalyst, which facilitates and generally speeds the rate at which chemical reactions proceed but does not alter the direction or nature of the reaction.

A "mutation" is a heritable change in genetic material, usually relative to a reference "wild-type" DNA sequence. Mutations can occur as a result of a single base change, multiple base changes, or the addition or deletion of more than one nucleotide to a DNA sequence, or rearrangement of larger sections of genes or chromosomes. Mutations can occur naturally or by human intervention and/or design. An "engineered mutation" refers to a mutation created by human design (e.g., the mutation did not spontaneously occur by natural causes and/or was the result of intentional human manipulation). A "genetically modified" or "engineered" cell/organism is a cell/organism whose genetic material has been altered by one or more engineered mutations (e.g., human induced mutations).

As used herein, the term "enhance," "increase," and/or "augment" generally refers to the act of improving a function or behavior relative to the unmodified, natural, expected or average. For example, a mutated (e.g., engineered) cell that has increased activity over that of the corresponding native/wild type cell, can have an improved activity (e.g. a faster rate of reaction, or occurrence of a measurable activity in the same amount of time) as compared to the activity of the corresponding wild type protein. Thus, as used herein, the term "increased external electron transport" refers to the transport of electrons from the internal space of the photosynthetic cell/organism outside the cell membrane in an engineered cell at higher levels (therefore providing an increased amount of electrons at the anode, and a corresponding higher signal) than a corresponding wild type cell/organism (e.g., a substantially equivalent photosynthetic cell/organism that is not engineered according to the present disclosure (e.g., not mutated/transfected with a gene for an exogenous external electron transport protein) under substantially similar conditions.

Having defined some of the terms herein, the various embodiments of the disclosure will be described.

Description

Embodiments of the present disclosure include engineered photosynthetic cells or organisms, photosynthetic electrochemical systems capable of generating an electric current using light induced photo-electrochemical reactions catalyzed by engineered photosynthetic cells/organisms, and photosynthetic electrochemical fuel cells capable of generating a fuel using light induced photo-electrochemical reactions catalyzed by engineered photosynthetic cells/organism. The present disclosure also provides methods of using the photosynthetic cells/organisms, photosynthetic electrochemical systems and photosynthetic electrochemical fuel cells of the present disclosure.

As mentioned above, previous attempts to make photo bio-electrochemical cells (PBECs) and/or photosynthetic microbial fuel cells (PMFCs) with photosynthetic organisms, such as cyanobacteria, demonstrated limitations in current densities, which were lower than that of currently available solar and biofuel cells. In order to make them competitive against biofuel cell and photovoltaic technologies, the current densities of PBECs, such as cyanobacteria based PBECs, had to be improved. The methods, cells and systems of the present disclosure achieve increased current densities through the use of genetic engineering to confer photosynthetic cells/organisms with improved external electron transfer (EET).

The EET capacity of exoelectrogens is a function of their dissimilatory metal reducing properties in an anaerobic environment. Exoelectrogens such as *Geobacter* and *Shewanella* exhibit their dissimilatory metal reducing capability with the help of numerous c-type cytochromes that are present on their outer membrane called outer membrane cytochromes (Omc), which execute electron transfer across the cell membrane. Recently, detailed pathways by which these bacteria perform EET through their Omc were elucidated on both a biochemical and genetic basis. *Geobacter* sp. expresses an array of Omc when they are grown in medium containing insoluble terminal electron acceptors such as Fe(III) oxide and Mn(IV) oxide. Particularly, outer membrane cytochrome S (OmcS) plays a predominant role in EET in *Geobacter sulfurreducens*. The pili of *G. sulfurreducens* were found to be aligned with numerous OmcS that help transfer the electrons extracellularly. Cyanobacteria (CB), however, do not contain any of these Omc, and, therefore, are not on par with exoelectrogens for EET, despite their tremendous photosynthetic energy conversion ability with high internal quantum efficiency of ~100%. The methods and systems of the present disclosure combine the desired properties of both organisms in engineered organisms/cells with unique properties for photo-bio-electrochemical energy conversion.

Thus embodiments of the present disclosure provide an engineered photosynthetic cell or organism including an exogenous nucleic acid molecule encoding a non-native (e.g., not naturally occurring in the recipient photosynthetic cell) redox enzyme capable of extracellular electron transport so that when the redox enzyme is expressed in the transformed cell or organism the engineered photosynthetic cell or organism has increased extracellular electron transport compared to a corresponding wild-type cell or organism (e.g., a cell/organism that does not contain the exogenous nucleic acid encoding the non-native redox enzyme). This increased extracellular electron transport provides a greater flow of electrons to the electrode for generation of a higher electrical current. This translates to a greater/higher electrical current in a PBEC and/or a greater/more efficient fuel production in a PMFC.

In embodiments, the engineered photosynthetic cell/organism includes a promoter operatively linked to the exogenous nucleic acid molecule encoding the non-native redox enzyme, such that the redox enzyme is expressed in the cell or organism into which it is transformed. In embodiments, the promoter is selected from an inducible promoter, constitutive promoters, and the like. Inducible promoters were used in the Examples below to regulate expression under laboratory conditions; however, constitutive promoters, such as, but not limited to $P_{psbA}$ (Nair, U., et al. (2001). "Functional elements of the strong psbAI promoter of *Synechococcus elongatus* PCC 7942." *Journal of Bacteriology* 183 (5): 1740-1747, which is incorporated herein by reference), $P_{sc}$ (GeneArt Synechococcus Engineering Kits by Invitrogen life technologies USER GUIDE Publication number MAN0005339, which is incorporated herein by reference), Plastocyanin promoter (Jeamton, W., et al. (2011). "Phycocyanin promoter of Spirulina platensis controlling heterologous expression in cyanobacteria." *Journal of Applied Phycology* 23 (1): 83-88, which is incorporated herein by reference) can also be used for constitutive expression of heterologous genes in *S. elongates*, or other transformed photosynthetic cell/organism.

In embodiments, the engineered photosynthetic cell/organism also includes a selective marker and/or targeting sequence operatively linked to the nucleic acid molecule encoding the redox enzyme. Selective markers are known in the art and facilitate identification of successfully transformed cells/organism, because the selective marker is operably linked to the exogenous nucleic acid molecule, such that expression of the selective marker (e.g., by a detectable signal) indicates that the organism/cell also contains and can express the exogenous nucleic acid molecule encoding the non-native redox enzyme. In organisms, targeting sequences can help direct the location and/or expression of the exogenous nucleic acid in a desired cell type or location.

As discussed above, due to their photosynthetic efficiency, in embodiments the photosynthetic cell or organism that is engineered is a cyanobacterium. In embodiments the cyanobacterium can be, but is not limited to, species of cyanobacterium from the genera *Synechococcus* and *Synechocystis*. In embodiments, the cyanobacterium can be *Synechococcus elongatus* PCC7942 or *Synechocystis* sp. PCC6803. In other embodiments, the cyanobacterium can be *Synechococcus* sp. strain PCC7002 (Stevens, S. E. and R. D. Porter (1980). "Transformation in Agmenellum quadruplicatum." *Proceedings of the National Academy of Sciences of the United States of America—Biological Sciences* 77 (10): 6052-6056, which is hereby incorporated by reference herein), or other species/strain amenable to gene transformation.

In embodiments, the redox enzyme capable of extracellular electron transport that is transformed into the engineered photosynthetic cell/organism can be an electro active terminal reductase from an exoelectrogenic organism. Exoelectrogenic organisms include organisms such as those discussed above, that are capable of transferring electrons generated in the cell/organism to extracellular electron acceptors (such as an anode/anode composite, anode material, or other material coupled to an anode). Examples of suitable exoelectrogenic organisms as a source of the electro active terminal reductase include, but are not limited to, exoelectrogenic microorganism selected from the genus *Geobacter* or *Shewanella*. In embodiments, the electro active terminal reductase can be an outer membrane cytochrome (Omc). In embodiments, the redox enzyme is outer membrane cytochrome S (OmcS) from *Geobacter sulfurreducens*. In embodiments, the OmcS enzyme is encoded by a nucleic acid sequence having SEQ ID NO: 3 or a nucleic acid sequence having at least 75% sequence identity with SEQ ID NO: 3 (including intervening ranges, such as 80% sequence identity, 90% sequence identity, 95% sequence identity, and so forth) and encoding a derivative of OmcS having the capability of extracellular electron transport. In embodiments, the OmcS enzyme includes the peptide sequence of SEQ ID NO: 4 or a peptide sequence having at least 75% sequence identity with SEQ ID NO: 3 (including intervening ranges, such as 80% sequence identity, 90% sequence identity, 95% sequence identity, and so forth) and retaining the capacity for extracellular electron transport.

In other embodiments, the redox enzyme is an outer membrane cytochrome from *G. sulfurreducens* such as OmcB (Leang, C., et al. (2003). "OmcB, a c-type polyheme cytochrome, involved in Fe(III) reduction in *Geobacter sulfurreducens*." *Journal of Bacteriology* 185 (7): 2096-2103, which is hereby incorporated by reference herein), OmcZ (Inoue, K., et al. (2010). "Purification and Characterization of OmcZ, an Outer-Surface, Octaheme c-Type Cytochrome Essential for Optimal Current Production by *Geobacter sulfurreducens*." *Applied and Environmental Microbiology* 76 (12): 3999-4007, which is hereby incorporated by reference herein) and OmcE (Mehta, T., et al. (2005). "Outer membrane c-type cytochromes required for Fe(III) and Mn(IV) oxide reduction in *Geobacter sulfurreducens*." *Applied and Environmental Microbiology* 71 (12): 8634-8641, which is hereby incorporated by reference herein), which are also involved in extracellular electron transfer.

In some embodiments, additional exogenous nucleic acid molecule(s) encoding one or more intermediate cytochromes capable of electron transfer to the outer membrane cytochrome (Omc) may also be included. In embodiments, the one or more intermediate cytochromes can be, but are not limited to, outer membrane cytochrome B (OmcB), MacA, and PpcA from *Geobacter sulfurreducens*, which can transfer electrons downstream to OmcS. In embodiments, additional cytochromes can be included in the engineered cell/organism. In embodiments, one or more cytochromes used to engineer the photosynthetic cell/organism include MtrABC and OmcA from *Shewanella* sp. In embodiments, one or more of the above cytochromes can be used to engineer the photosynthetic cell/organism.

In embodiments, the engineered photosynthetic cells/organisms of the present disclosure having one or more exogenous nucleic acid molecule(s) encoding one or more non-native redox enzymes and, optionally, one or more intermediate cytochromes have enhanced capacity for extracellular electron transfer due to the expression of the exogenous, non-native redox enzyme (e.g., a membrane cytochrome). An embodiment of an engineered photosynthetic cells and the greater capacity for extracellular electron transfer is illustrated in greater detail in Example 2, below.

In order to produce the engineered photosynthetic cells/organisms of the present disclosure, in embodiments, the photosynthetic cell/organism is transformed with an expression vector including the nucleic acid molecule encoding the non-native redox enzyme. In embodiments, the vector includes an expression cassette including the nucleic acid molecule encoding the non-native redox enzyme as well as the operably linked promoter and optional selective marker. In embodiments, a targeting sequence is operatively linked to the expression cassette to direct the insertion of the expression cassette (and, hence, the nucleic acid encoding the redox enzyme) into the recipient cell/organism.

In embodiments, the recipient cell/organism is a cyanobacterium, as described above. In embodiments, the redox enzyme is an Omc, such as, but not limited to, an Omc from a *Geobacter* species. In embodiments, the cyanobacterium is transformed with the expression vector including the nucleic acid molecule encoding an OmcS (e.g., an Omc from a *Geobacter* species), a promoter operatively linked to the nucleic acid encoding the OmcS, a nucleic acid encoding a selective marker operatively linked to the nucleic acid encoding the OmcS, and a targeting sequence directing insertion of the expression cassette into the cyanobacteria genome.

After transforming the recipient cells, successfully transformed cells/organisms are selected using methods known in the art, including, but not limited to selection via a selective marker (e.g., growth on a selective media, fluorescence, and the like) co-transformed with the target redox gene. For instance, if the selective marker is an antibiotic resistance gene, cells can be grown on selective media (e.g., media including the antibiotic) and positive cultures can be selected. In embodiments, further screening can be done to confirm that the exogenous nucleic acid has been successfully incorporated into the recipient cell/organism.

Embodiments of the present disclosure also include anodes for a photo-bioelectrochemical cell (PBEC) or a photosynthetic microbial fuel cell (PMFC) including the engineered photosynthetic organisms/cells of the present disclosure. In embodiments, the anodes of the present disclosure include an anode material, one or more engineered photosynthetic cells or organisms according to the present disclosure as described above having an exogenous nucleic acid molecule encoding a non-native redox enzyme capable of extracellular electron transport, and a nanostructured material in electrochemical communication with the engineered photosynthetic organism or cell. In embodiments, the engineered photosynthetic organism or cell can oxidize water molecules and generate electrons using a light induced photo-electrochemical reaction wherein at least a portion of electrons generated by the photosynthetic organism or cell are transferred to the anode material via direct electron transfer. Due to the presence of the exogenous redox enzyme, the engineered cells on the anode transfer more electrons out of the cell to the anode than a corresponding non-engineered (wild type) cell/organism.

In embodiments, the nanostructured material comprises a matrix of nanostructured material that couples the photosynthetic organism or cell to the anode. In embodiments, the matrix of nanostructured materials can be, but is not limited to, carbon nanostructured materials, metallic nanoparticles, semiconductor nanoparticles, quantum dots and combinations of these materials. In embodiments, examples of suitable carbon nanostructured materials include, but are not limited to, carbon nanotubes, multi-walled carbon nanotubes, fullerenes, carbon nanoparticles, graphenes, two-dimensional carbon nanosheets, graphite platelets, and combinations of these materials. In some embodiments the matrix of nanostructured material is multi-walled carbon nanotubes.

In embodiments, the anode material can be a firm or flexible substrate for supporting the matrix of nanostructure material. In embodiments, the anode material includes conducting materials to conduct the electrons generated by the engineered photosynthetic cell/organism and transferred to the electrode material from the cell/organisms and/or via the nanostructured material. In embodiments, conducting materials for the anode can include, but are not necessarily limited to, carbon, metal, semiconductor, and combinations thereof, wherein the conducting materials are in bulk form, nanostructure form, or a combination thereof. In other embodiments, the anode material/substrate can be a non-conducting material, but something capable of supporting a conducting material, such as a matrix of nanostructured material. For instance, in embodiments, the anode is a carbon paper anode including paper printed with multi-walled carbon nanotubes (CNT). In embodiments, the anode is another substrate modified with CNT or other nanostructure matrix material. In embodiments, the anode can be a carbon brush, such as a Mill-Rose™ carbon brush, which provides more surface area than carbon paper anodes and are employed in microbial fuel cells. As used herein, the combination of anode material/substrate, matrix of nanostructured material, and engineered photosynthetic organism may be (as a whole) referred to as the anode or as an anode composite.

In embodiments the engineered photosynthetic organism or cell self-adheres to the nanostructured material or grows/forms a biofilm on the nanostructured material. In some embodiments, the engineered photosynthetic organism or cell is coupled to the nanostructured material by a linking agent. The linking agent can be anything capable of physically and/or chemically linking the organism/cell to the nanostructured material such that electrodes generated by the engineered photosynthetic organism/cell can be transferred to the nanostructured material. In some embodiments including a linking agent, the linking agent can be, but is not limited to, 1-pyrenebutanoic acid succinimidyl ester (PBSE), a protein homo-bifunctional cross-linking agent, a hetero-bifunctional cross-linking agent, and combinations thereof.

The anodes of the present disclosure described above can be included in a biochemical cell, such as a 3 electrode cell, for various purposes. In embodiments, the anode can be included in a PBEC or a PMFC to generate an electric current or an alternative fuel, respectively.

In embodiments, the present disclosure provides a photo-bioelectrochemical cell (PBEC) including an anode/anode composite of the present disclosure as described above (including the engineered photosynthetic cell/organism of the present disclosure) and a cathode composite including a cathode and at least one enzyme or metallic catalyst capable of reducing a reductant.

Although the engineered photosynthetic cells/organisms of the present disclosure are capable of direct electron transfer of photosynthetically generated electrons to the anode/nanostructured matrix material, in embodiments, a redox mediator can also be included in and electrochemical cell, PBECs or PMFCs of the present disclosure. In embodiments, the mediator can be, but is not limited to, ferricyanide, a quinone-based compound, an osmium complex based compound, a redox chemical compound, and combinations thereof.

As discussed above for the anode, in embodiments, the cathode includes conducting materials. In embodiments, such conducting materials can include, but are not necessarily limited to, carbon, metal, semiconductor, and combinations thereof, wherein the conducting materials are in bulk form, nanostructure form, or a combination thereof. In embodiments, the cathode composite can also include matrix of nanostructured material coupling at least one enzyme or metallic catalyst capable of reducing the reductant to the cathode. In embodiments, the cathode material can be a rigid or flexible substrate for supporting the matrix of nanostructured material, and may be a conducting or non-conducting material. In embodiments, the matrix of nanostructured material for the cathode is as described above for the anode.

Embodiments of the present disclosure include photobioelectrochemical cells (PBECs) having an anode of the present disclosure including engineered photosynthetic cells/organisms as described above, and a cathode capable of reducing a reductant. In embodiments, the reductant is $O_2$. In embodiments, the cathode includes at least one enzyme or metallic catalyst capable of reducing $O_2$. Embodiments of metallic catalysts capable of reducing include, but are not limited to, platinum. In embodiments of a PBEC of the present disclosure, at least one enzyme capable of reducing $O_2$ can be, but is not limited to, laccase, bilirubin oxidase, ascorbate oxidase, tyrosinase, catechol oxidase, and combinations thereof.

The present disclosure also includes methods of generating an electrical current using the engineered photosynthetic cells/organisms of the present disclosure, the anodes of the present disclosure, and the PBECs of the present disclosure. Embodiments of methods of the present disclosure for generating an electrical current include providing a PBEC of the present disclosure including an anode as described above and a cathode composite including a cathode and at least one enzyme or metallic catalyst capable of reducing $O_2$ and exposing the PBEC to light in the presence of water. Upon exposure to light and water, the engineered photosynthetic cell(s)/organism(s) uses light energy to oxidize a water molecule and generate electrons, which are transferred out of the cell (at least some of them transferred via the non-native redox enzyme, such as, but not limited to an outer membrane cytochrome) and to the anode via the nanostructured material. These electrons generated at the anode reduce $O_2$ at the cathode, thereby inducing a potential difference between the anode and the cathode and generating an electrical current.

The present disclosure also includes photosynthetic microbial fuel cells (PMFCs) having an anode of the present disclosure including an engineered photosynthetic cells/organisms as described above, and a cathode composite including a cathode capable of reducing $H^+$ to produce $H_2$. Also included in the present disclosure are methods of generating $H_2$ fuel. In embodiments, methods of generating $H_2$ include providing a PMFC of the present disclosure including an anode as described above and a cathode composite including a cathode and at least one enzyme or metallic catalyst capable of reducing $H^+$ to produce $H_2$. An example of an enzyme capable of reducing $H^+$ to produce $H_2$ includes, but is not limited to hydrogenase enzymes. Upon exposing the PMFC to light in the presence of water, the engineered photosynthetic cell(s) or organism(s) uses light energy to oxidize a water molecule and generate electrons, at least some of which are transferred out of the cell (e.g., via the non-native redox enzyme or natural routes) to the anode via the nanostructured material. The electrons generated at the anode reduce $H^+$ at the cathode, thereby generating $H_2$.

The examples below describe embodiments of the present disclosure including genetically engineered heterologous omcS in *Synechococcus elongatus* PCC7942 to enhance the cyanobacterial extracellular electron transfer to alternate electron acceptors. The examples represent embodiments using genetically engineering highly efficient photosynthetic organisms, such as, but not limited to, cyanobacteria, for enhancing EET as described above.

Additional details regarding the methods and compositions of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. Publications are incorporated by reference only where indicated by notation in the text, such references are incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Now having described the embodiments of the present disclosure, in general, the following Examples describe some additional embodiments of the present disclosure. While embodiments of present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

This Example describes an endeavor to provide highly efficient light to electricity conversion in an embodiment of a photosynthetic biological Grätzel cell of the present disclosure (FIG. 1) using photoelectric organisms without genetic modification. First, high photoelectrochemical energy conversion using live, wild-type cyanobacteria (CB) cells was demonstrated.

Experimental Procedure

Two different commercially available, wild-type CB strains, *Nostoc* sp. ATCC27893 and *Anabaena variabilis* ATCC29413 were obtained.

Anodes modified with a matrix of nanostructured material (provided by carbon nanotubes (CNTs)) were prepared as briefly described as follows. SpectraCarb 2050-L carbon paper (CP) was used as the base electrode. The CP was treated with a boiling mixture of 1 M nitric acid and 0.5 M sulfuric acid (1:4 ratio) for an hour and washed with double distilled water. The CNT solution (1 mg/mL) was prepared in dimethyl formamide and suspended to form a uniform slurry by sonicating it for 15 minutes in an ultrasonic homogenizer. 5 mL of CNT was drop-cast on the CP, dried in an oven to make a CNT modified CP.

Each CB species were immobilized separately on the CNT modified anodes to serve as photo-catalysts as described in detail in N. Sekar, Y. Umasankar and R. P. Ramasamy, *Physical Chemistry Chemical Physics*, 2014, 16, 7862-7871, which is hereby incorporated by reference herein. Briefly, the fresh cyanobacterial culture was washed using phosphate buffer (100 mM, pH 7) and re-suspended in the same buffer. 5 µL of the culture was loaded onto CNT modified CP and allowed to air dry at room temperature. The CNT modified CP was used as the anode for the electrochemical experiments.

A laccase-CNT modified cathode was used for $O_2$ reduction in PBEC. The 5 mg/ml laccase enzyme solution was prepared by dissolving laccase (laccase from *Trametes versicolor* in powder form purchased from Sigma Aldrich) in phosphate buffer and immobilized onto CNT modified glassy carbon electrode using the tethering agent 1-pyrenebutanoic acid, succinimidyl ester (PBSE). By using site specific electron transfer inhibitors (indicated with numbered stars (1-4) in FIG. 2A), likely routes for e-transfer between the CB and the electrode were identified.

Results and Discussion

Figure 2A:
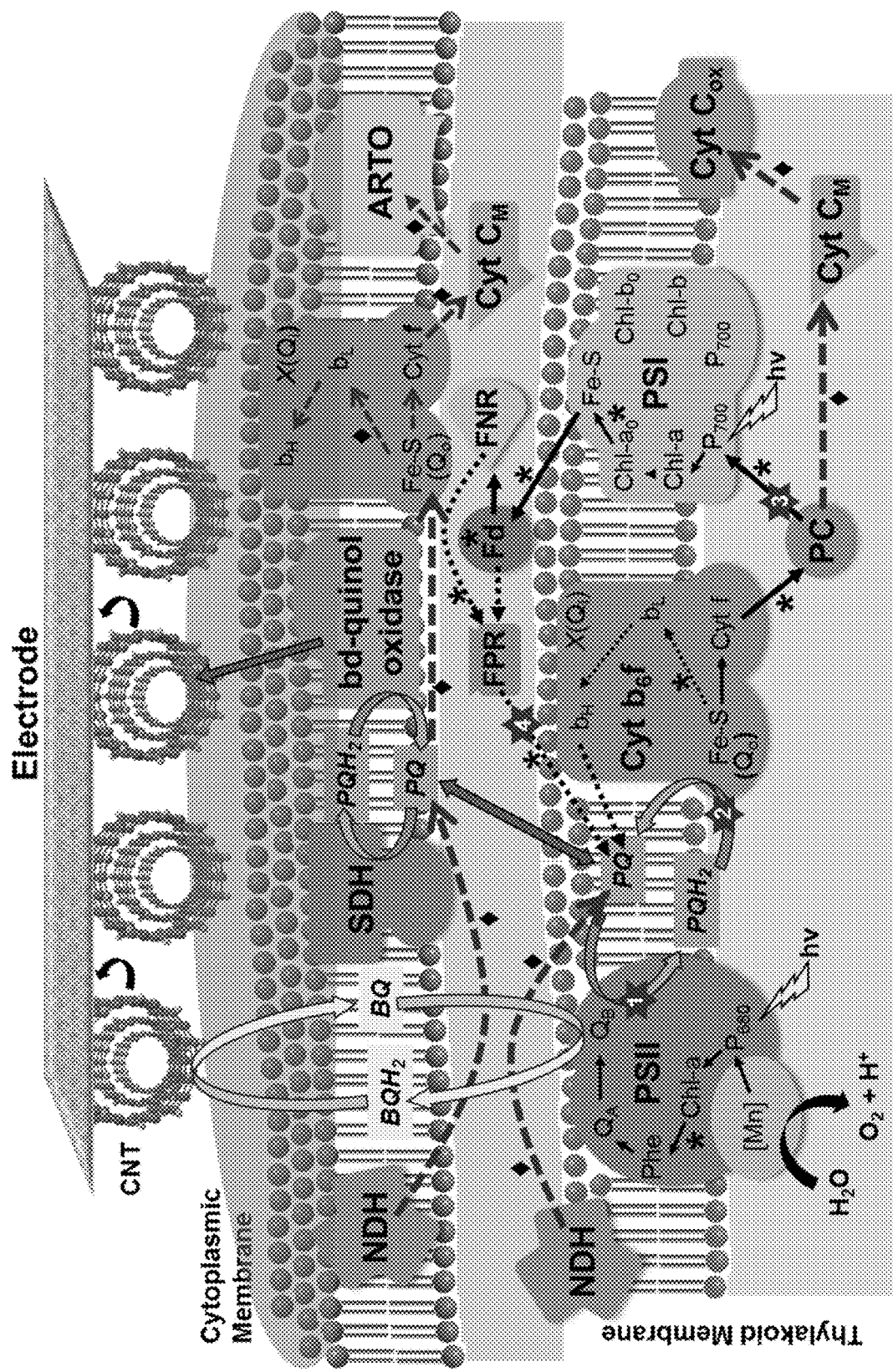
FIG. 2A illustrates Photosynthetic (arrows/pathways marked with *) and respiratory (arrows/pathways marked with ♦) electron transport chain in cyanobacteria (note: for pathways within a larger shape, the * and ♦ symbol are used once and indicate the entire pathway). The block arrows represent e-harvesting pathways for electricity generation. The above pathways were established using site-specific inhibitors 1-4 indicated by large stars.

Through this work, it was demonstrated that power generation occurred even during dark, similar to that of microbial fuel cells. This is believed to be because the plastoquinone (PQ) pool is shared by both the cytoplasmic (respiration) and thylakoid (photosynthesis) membranes as shown in FIG. 2A, making it easier for bd-quinol oxidase (bdQox) and/or other redox protein on the outer membrane to transfer e- out of the cell both in light and dark conditions.

Figure 2B:
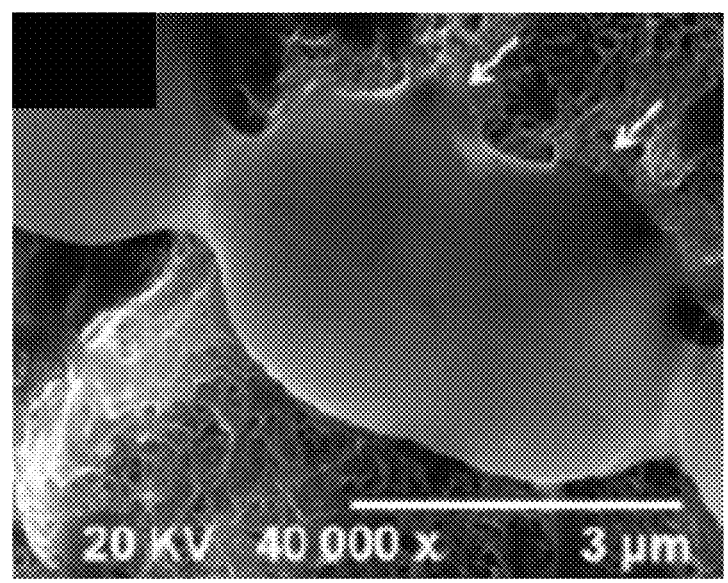
FIG. 2B is an SEM image of CB cells immobilized on CNT modified electrodes.
Figure 2C:
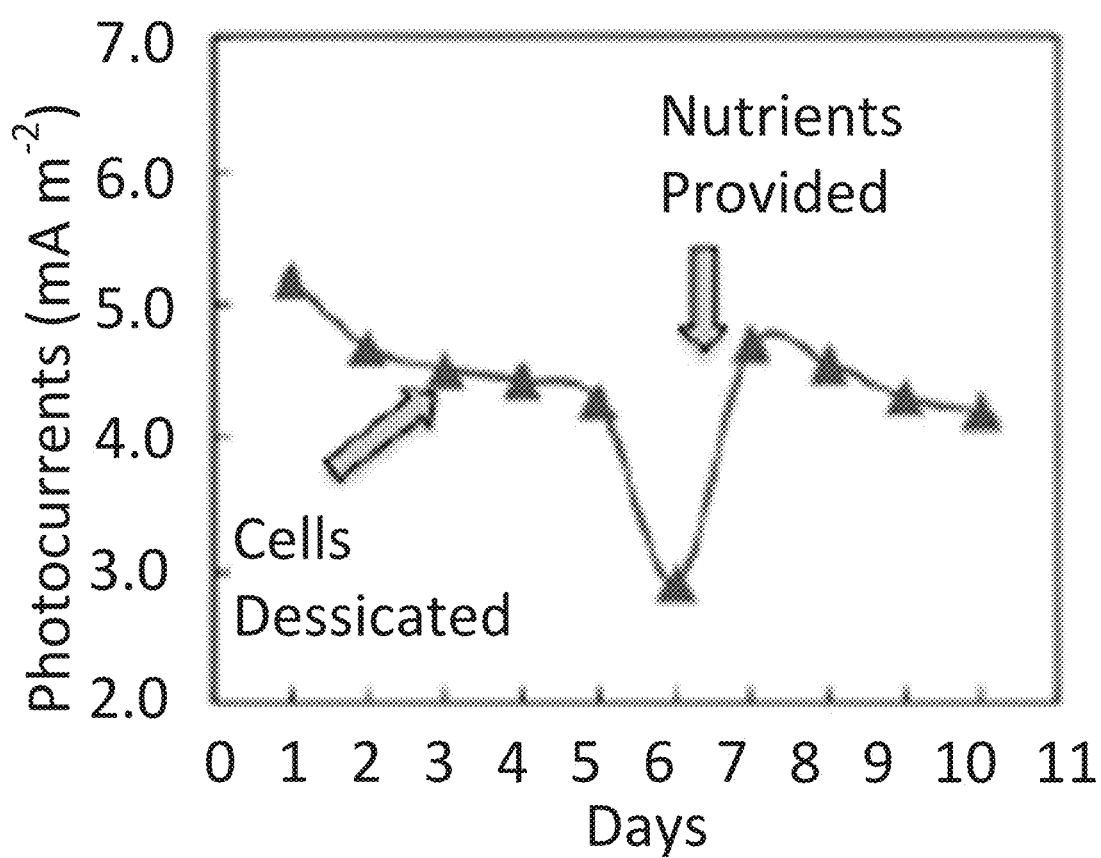
FIG. 2C is a graph illustrating photo-activity recovery after desiccated CB cells were replenishment with nutrients indicating long-term stability.
Figure 2D:
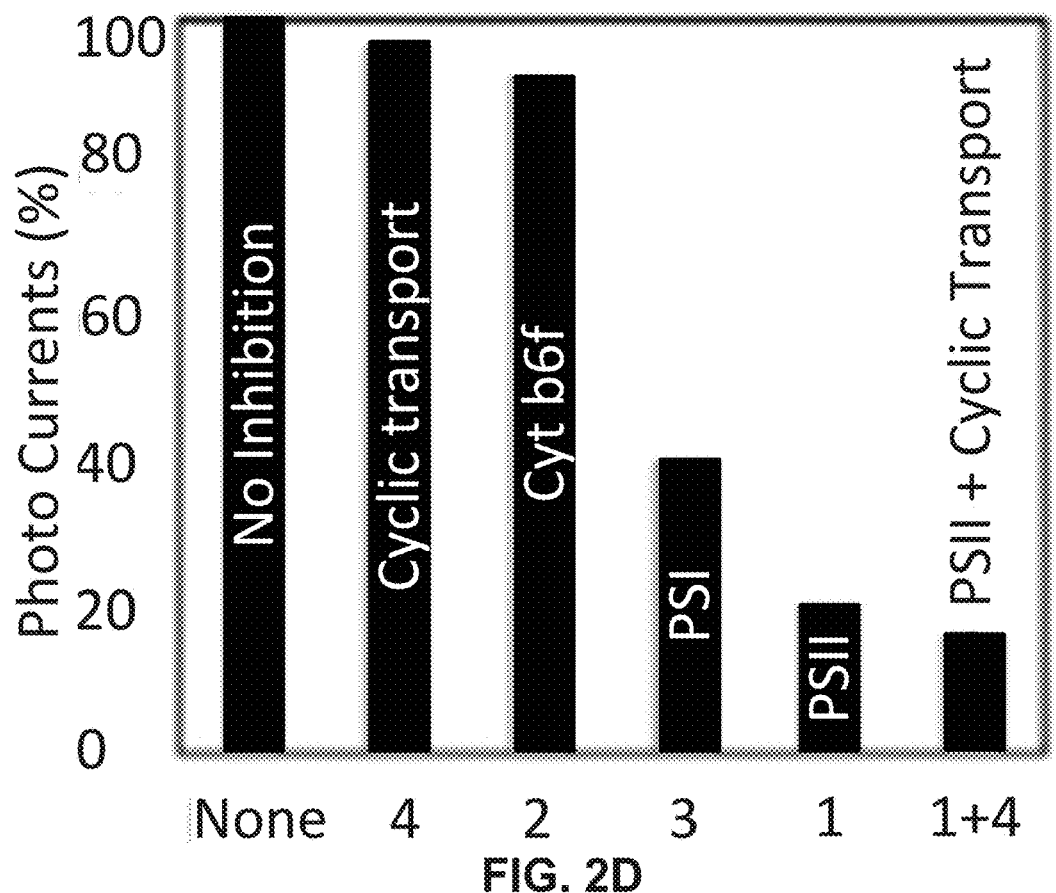
FIG. 2D is a bar graph illustrating loss of photocurrents when e-transfer was inhibited at sites 1-4.

It was also shown that direct electron transfer (DET) was not as facile as the mediated electron transfer (MET) using benzoquinone (BQ) (block arrows in FIG. 2A), likely due to poor bdQox-electrode interaction compared to that of typical OmcS-electrode interaction in *Geobacter* sp. It was further determined that CNTs can penetrate into the cell membrane for intimate attachment as illustrated by the image in FIG. 2B. Photocurrent stability was also shown to be excellent as long as the CB cells are fed with at least minimal nutrients needed for survival, as illustrated in FIG. 2C showing cells becoming desiccated prior to supplying fresh nutrients. Water oxidation at PSII was shown to provide the main source for e- as determined by the loss of photoactivity when PSII was inhibited as illustrated in FIG. 2D.

Figure 2E:
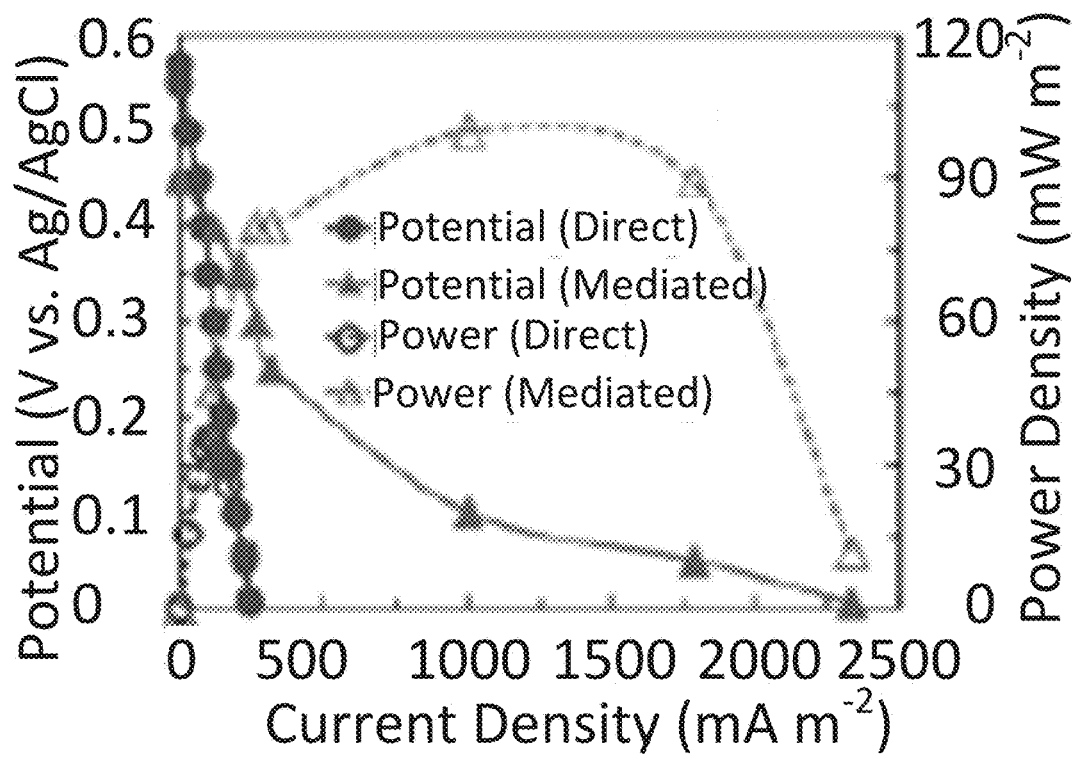
FIG. 2E is a graph illustrating power density and polarization profiles for direct and mediated transport.

The CB cell-based photosynthetic microbial fuel cell (PBEC) of this example generated power density of about 35 and 100 mW/m$^2$ for direct and mediated operation (FIG. 2E). The results demonstrated that nutrient-rich CB cells can exhibit higher stability on the electrodes than isolated photosynthetic organelles and offer more ways to harvest electrons.

Example 2

Although photosynthetic microorganisms such as cyanobacteria exhibit light dependent electrogenic characteristics in photo bio-electrochemical cells (PBECs) and/or photosynthetic microbial fuel cells (PMFCs) that generate substantial photocurrents, as discussed above, the generated current densities are lower than their photovoltaic counterparts. Example 1 above demonstrated that a cyanobacterium *Nostoc* sp. employed in PBEC could generate up to 35 mW m$^{-2}$ even in a non-engineered PBEC.

The present example describes novel and successful genetic engineering of cyanobacteria to further enhance its extracellular electron transfer. The cyanobacterium *Synechococcus elongatus* PCC7942 was genetically engineered to express a non-native redox protein called outer membrane cytochrome S (OmcS) (N. Sekar, R. Jain, Y. Yan and R. P. Ramasamy, *Biotechnology and Bioengineering*, 2016, 113, 675-679, which is hereby incorporated by reference herein). OmcS is predominantly responsible for metal reducing abilities of exoelectrogens such as *Geobacter* sp. As described below, the engineered *S. elongatus* exhibited higher extracellular electron transfer ability resulting in ~9 fold higher photocurrent generation on the anode of a PBEC than the corresponding wild-type cyanobacterium.

Experimental Procedure

The wild type *Synechococcus elongatus* PCC7942 was used as a model organism for the present example. Both the wild-type (Wild-CB) and the genetically engineered *S. elongatus* (Eng-CB) were grown in modified BG11 medium as described in N. Sekar, Y. Umasankar and R. P. Ramasamy, *Physical Chemistry Chemical Physics*, 2014, 16, 7862-7871, which is hereby incorporated by reference herein. The cyanobacterial cultures were inoculated in the autoclaved media and grown at 30±2° C. at 100 rpm under continuous illumination using fluorescent lamps (80 µmol m$^{-2}$ s$^{-1}$). The coding sequence of omcS gene from *G. sulfurreducens* PCA strain (NC_002939.5) was codon optimized for expression in *S. elongatus* and synthesized by Genscript. Both the nucleotide sequence for the coding optimized omcS gene (SEQ ID NO: 3) and the encoded OmcS peptide sequence (SEQ ID NO: 4) are provided below.

Figure 3A:
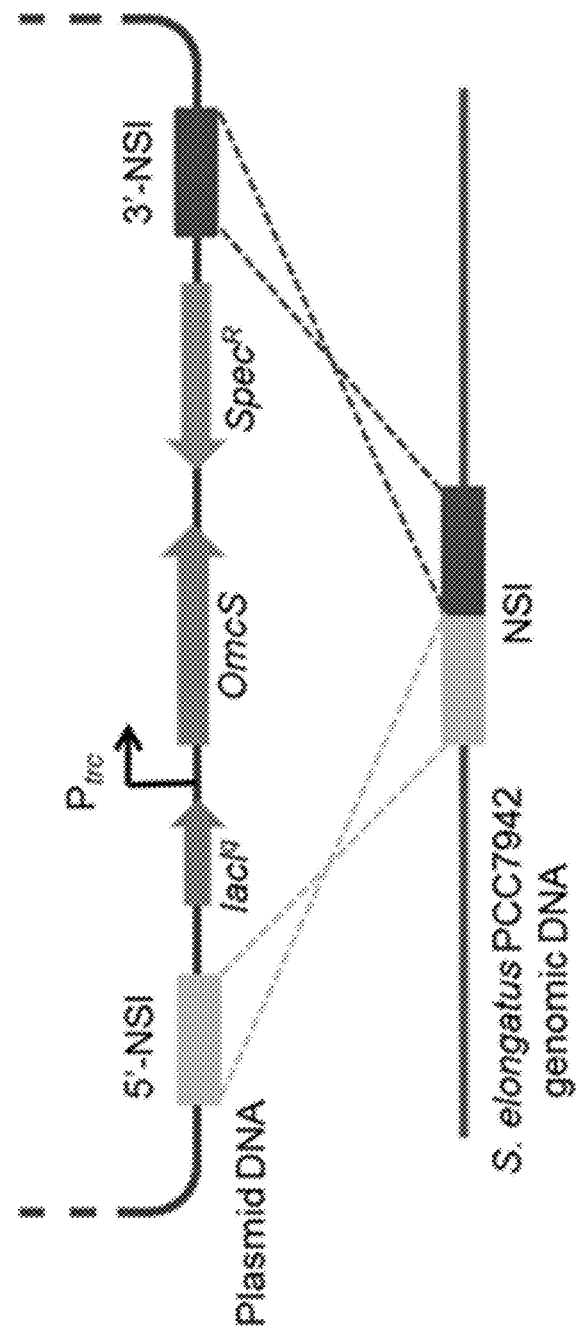
FIGS. 3A and 3B illustrate chromosomal integration of omcS in *S. elongatus* to produce an embodiment of a genetically engineered *S. elongatus* cyanobacteria (Eng-CB).

The vector pNR1 was constructed by cloning the omcS gene into neutral site I (NSI) targeting pAM2991 vector (N. B. Ivleva, M. R. Bramlett, P. A. Lindahl and S. S. Golden, *Embo Journal*, 2005, 24, 1202-1210, which is hereby incorporated by reference herein) that harbors spectinomycin resistance gene (specR) as an antibiotic selection marker as illustrated in FIG. 3A. The expression of omcS gene was under the control of $P_{trc}$, and was inducible by the addition of isopropyl β-D-1-thiogalactopyranoside (IPTG). The vector pNR1 was transformed into *S. elongatus* PCC7942 following the transformation protocol given by Invitrogen, Life Technologies. The colonies were screened in BG11-agar plates with 50 µg/ml spectinomycin, and the presence of omcS in the positive colonies was confirmed by PCR using the primers: 5'GGGAAAGAAT-TCGAAGGAGTATACCTATACATGAAGAAAGGCAT-GAAAGTTAGTCTGA 3' (SEQ ID NO: 1) and 5'GGGAAAGGATCCTTAATCTTTGGCGTGGCAT-TTGTTAC 3' (SEQ ID NO: 2). The Eng-CB (*S. elongatus* CB engineered to include the omcS gene from *G. sulfurreducens*) was grown in modified BG11 and was induced at an $OD_{750}$ of 0.6 with 1 mM IPTG. The sample was collected after 24 hrs for heme staining in non-denaturing SDS-PAGE as explained by Thomas et al. (*Analytical Biochemistry*, 1976, 75, 168-176), which is hereby incorporated by reference herein.

Ferricyanide reduction assay was carried out to evaluate the extracellular electron transfer of the cyanobacterium. Both the Wild-CB and the Eng-CB cultures were harvested at an OD750 of 0.6 by centrifuging the cells at 5000 rpm for 10 minutes at room temperature and re-suspended in fresh BG11 medium. Following induction with 1 mM IPTG, 1 mM potassium ferricyanide (in BG11 medium) was added, and the culture was split into two halves. One half was incubated in light, and the other was covered with aluminum foil and incubated in dark to assess the reduction of potassium ferricyanide in both light and dark conditions. Samples were collected every 4 hours for 48 hours. The chlorophyll content of the samples was measured from the absorbance at 680 nm. The sample was centrifuged at 10,000 rpm for 5 minutes at room temperature, and the absorbance of supernatant was measured at 420 nm to calculate the concentration of residual potassium ferricyanide. The rate of ferricyanide reduction for 12 hours was then normalized with the average chlorophyll content as described in Bradley et al. (*Physical Chemistry Chemical Physics*, 2013, 15, 13611-13618), which is hereby incorporated by reference herein.

Electrochemical experiments were conducted with Wild-CB and Eng-CB to investigate the photocurrent generation. Briefly, the cells were harvested by centrifugation and drop-casted onto carbon paper (CP) modified with multi-walled carbon nanotubes (CNT) as described in Sekar, et al. (2014), incorporated by reference above. The same amount of cells was drop-casted onto the electrode for comparing the performance of Wild-CB and Eng-CB. Half-cell electrochemical system with either CP/CNT/Wild-CB or CP/CNT/Eng-CB as working electrode, Ag/AgCl, sat. KCl as reference electrode and platinum wire as counter electrode was employed to measure open circuit potential (OCP) and current generated at an applied voltage using CHI potentiostat (401a models, CH Instruments Inc). All potentials reported here are with respect to Ag/AgCl electrode. 100 mM potassium phosphate buffer (pH 7) was used as electrolyte. A Dolan-Jenner Industries Fibre-Lite lamp (model 190) with a light intensity of 76 mW cm$^{-2}$ was used for illumination.

Results and Discussion

Figure 3B:
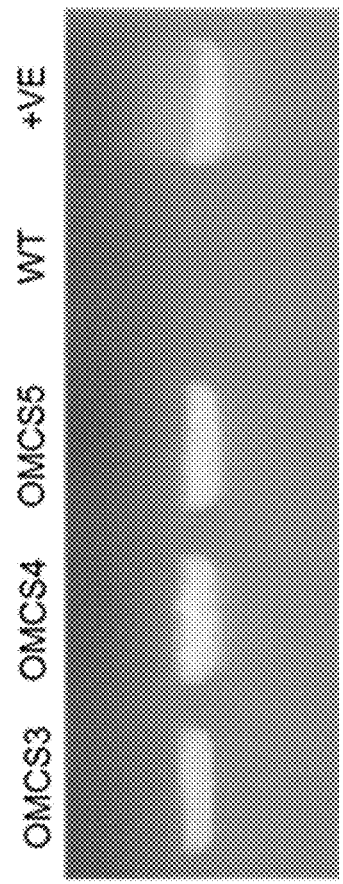

*S. elongatus* PCC7942 was the first cyanobacterium demonstrated to be reliably transformable by exogenously added DNA as described by Shestako, et al. (1970). Following transformation, omcS was integrated into the NSI site in genomic DNA of *S. elongatus* by homologous recombination as shown in FIG. 3A. The presence of omcS in the *S. elongatus* was evident from its ability to grow in the spectinomycin BG11 agar plates and was confirmed subsequently by PCR (FIG. 3B) using the primers given above (SEQ ID NOs: 1 and 2).

Figure 4B:
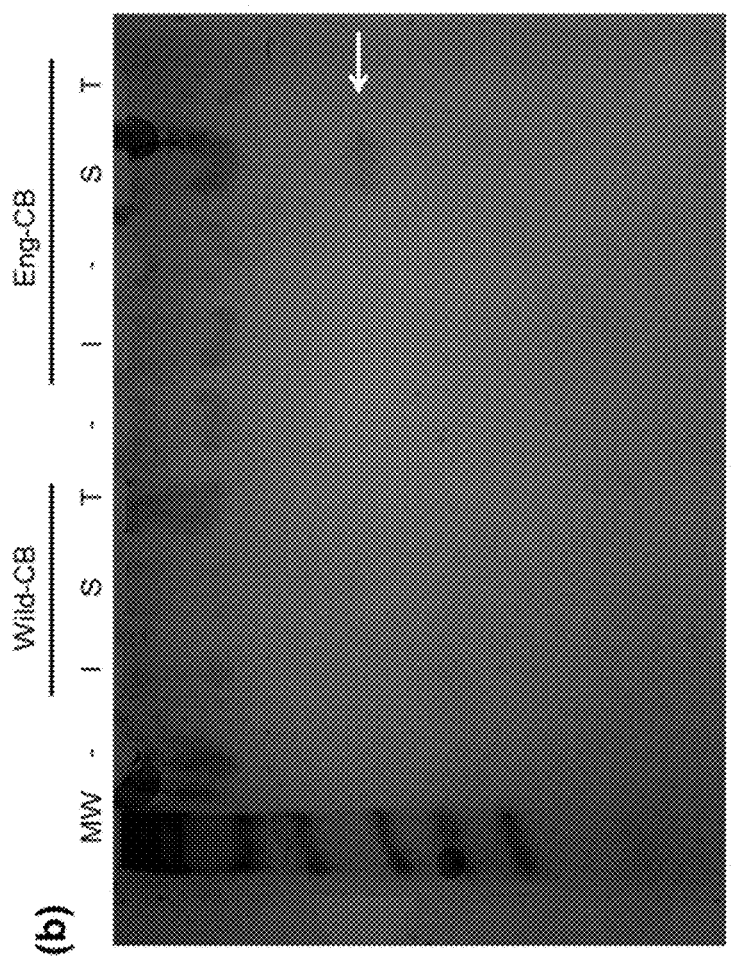
FIG. 4B is a digital image illustrating heme staining following the separation of total protein on non-denaturing polyacrylamide gel. MW: standard molecular weight marker; I: insoluble protein in the pellet; S: soluble protein in the supernatant; T: total protein (I+S). The white solid arrow represents the active OmcS in the soluble fraction of Eng-CB.
Figure 4A:
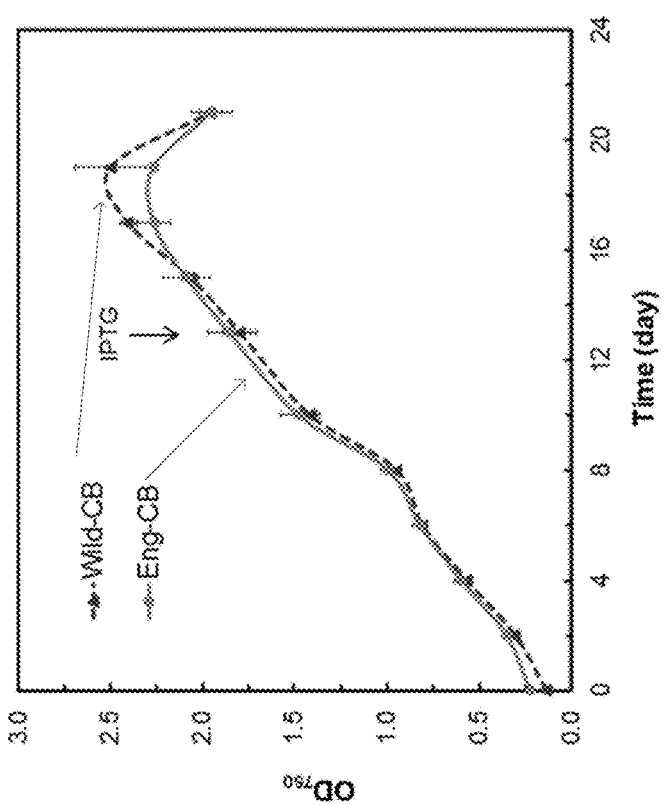
FIG. 4A is a graph illustrating a growth curve of Wild-CB or Eng-CB. Eng-CB culture was induced with 1 mM IPTG at $13^{th}$ hour.

The growth characteristic of Eng-CB was similar to that of Wild-CB implying that the expression of heterologous omcS has no detrimental effect on the cyanobacterium (FIG. 4A). The log phase Eng-CB culture ($OD_{750}$ of ~0.6) was induced with IPTG (1 mM), and expression of omcS was confirmed in non-denaturing PAGE followed by heme staining (FIG. 4B) which specifically stains multi-heme proteins such as OmcS. The heme staining confirmed that the OmcS was active, because the appearance of a distinct band on the activity gel was solely based on peroxidase activity of the active heme protein. The significant band was seen only in the soluble fraction of Eng-CB, but not in the insoluble fraction, which is meaningful considering the fact that OmcS is not an integral membrane protein but a peripheral membrane protein that is loosely attached to the outer membrane. However, the precise localization of OmcS has yet to be confirmed by specifically analyzing the various membrane fractions.

Figure 5A:
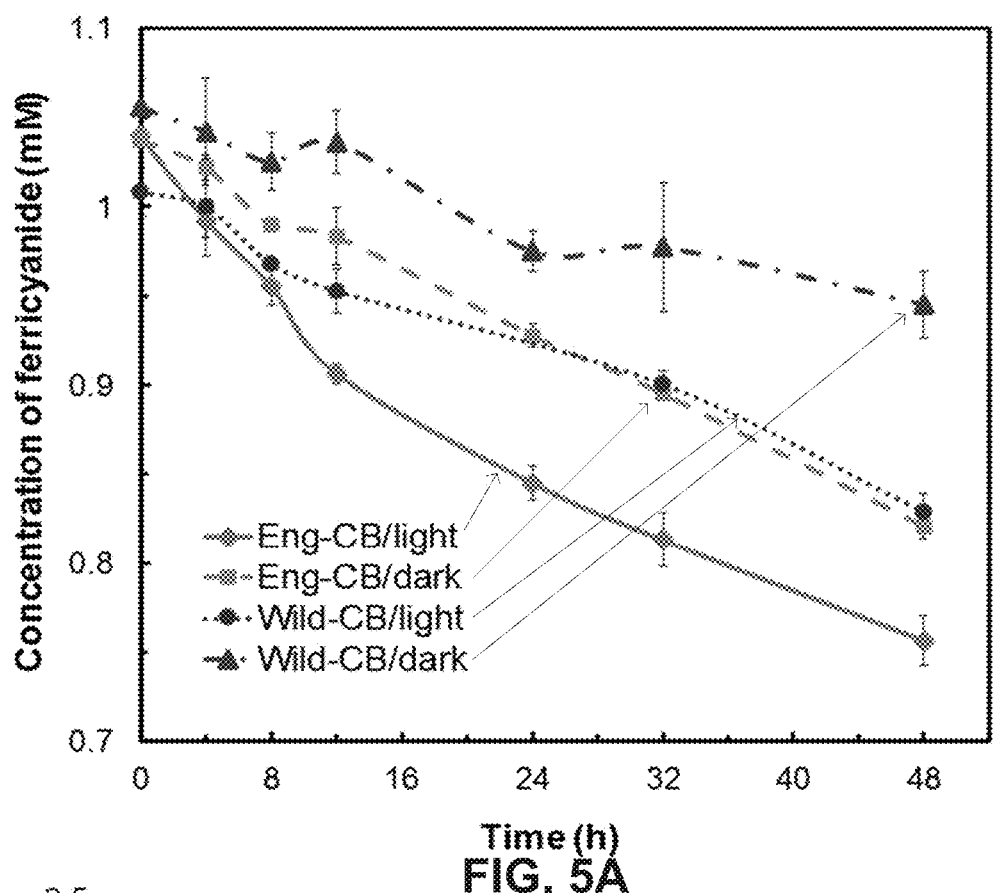
FIG. 5A is a graph illustrating reduction of potassium ferricyanide to ferrocyanide by Wild-CB and Eng-CB over 48 hours in both light and dark conditions.

Upon confirming the expression of active omcS, the ability of Eng-CB to reduce the exogenously added potassium ferricyanide was studied and compared with that of Wild-CB. Being highly water soluble, ferricyanide cannot cross the outer membrane of cyanobacteria and is highly appropriate to study direct electron transfer (DET). Thus, the rate of ferricyanide reduction of Wild-CB and Eng-CB was measured in both light and dark condition as shown in FIG. 5A. Although potassium ferricyanide is light sensitive, it was found to be more stable without any significant reduction during the short period of our control experiments in the absence of cyanobacterium under light condition. Cyanobacteria such as *S. elongatus* is known to exhibit light dependent electrogenic activity in the presence of various redox mediators such as hydroxyl napthoquinone (Yagishita, et al. (1993) and dimethyl benzoquinone (Tsujimura, et al. (2001). Both Wild-CB and Eng-CB strains reduced ferricyanide under light as well as dark conditions (FIG. 5A). The ferricyanide reduction in the light and dark was attributed to the electrons channeling from photosynthetic (PETC) and respiratory electron transport chain (RETC), respectively. The rate of ferricyanide reduction by Eng-CB in light was found to be ~2 fold higher than that of Wild-CB in light (FIG. 5B), which clearly corroborates that the heterogeneously expressed omcS enhanced the EET in the Eng-CB. Further, it is also interesting to note that the rate of ferricyanide reduction of Eng-CB in dark was also observed to be ~2.5 fold higher compared to that of Wild-CB in dark (FIG. 5B), providing evidence that the OmcS interacted with both the PETC and RETC.

Figure 6A:
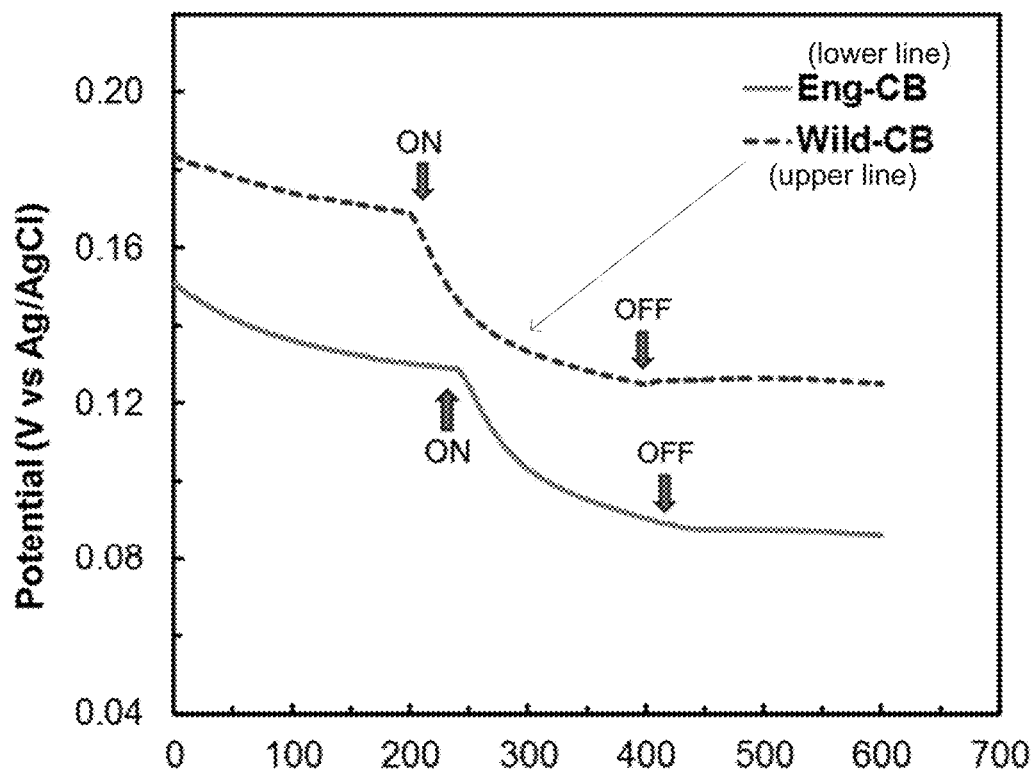
FIGS. 6A and 6B illustrate measurement of open circuit potential (OCP) of the electrode with Wild-CB or Eng-CB using Ag/AgCl as a reference electrode in light and dark phases (FIG. 6A) and measurement of current generated by Wild-CB and Eng-CB by applying an over-potential of 0.1 V (vs Ag/AgCl) in light and dark phases (FIG. 6B).

The photocurrent generation by the genetically modified *S. elongatus* was investigated using amperometric i-t curve in a photo bio-electrochemical half-cell using the cyanobacterial anode as explained in the experimental procedure. The electrode harboring Eng-CB showed a lower open circuit potential (OCP) compared to that of Wild-CB, which is indicative of Eng-CB being a better anode (FIG. 6A). Once light is turned on, the OCP significantly reduced in both Eng-CB and Wild-CB, which is consistent with the observation in *Nostoc* sp., above. Upon absorbing light energy, the redox potential of both PSII and PSI reaches a more negative value from ~+0.1V to ~-0.1 V for PSII and from ~+0.2 V to ~-1.4 V for PSI (all redox potentials are expressed with respect to Ag/AgCl) and is solely responsible for the decrease in OCP during the light phase. Similarly, upon shutting off the light, the OCP stabilized in both Eng-CB and Wild-CB, which illustrated that the response can be primarily attributed to the photo-electrochemical reactions of cyanobacteria on the electrode.

Figure 6B:
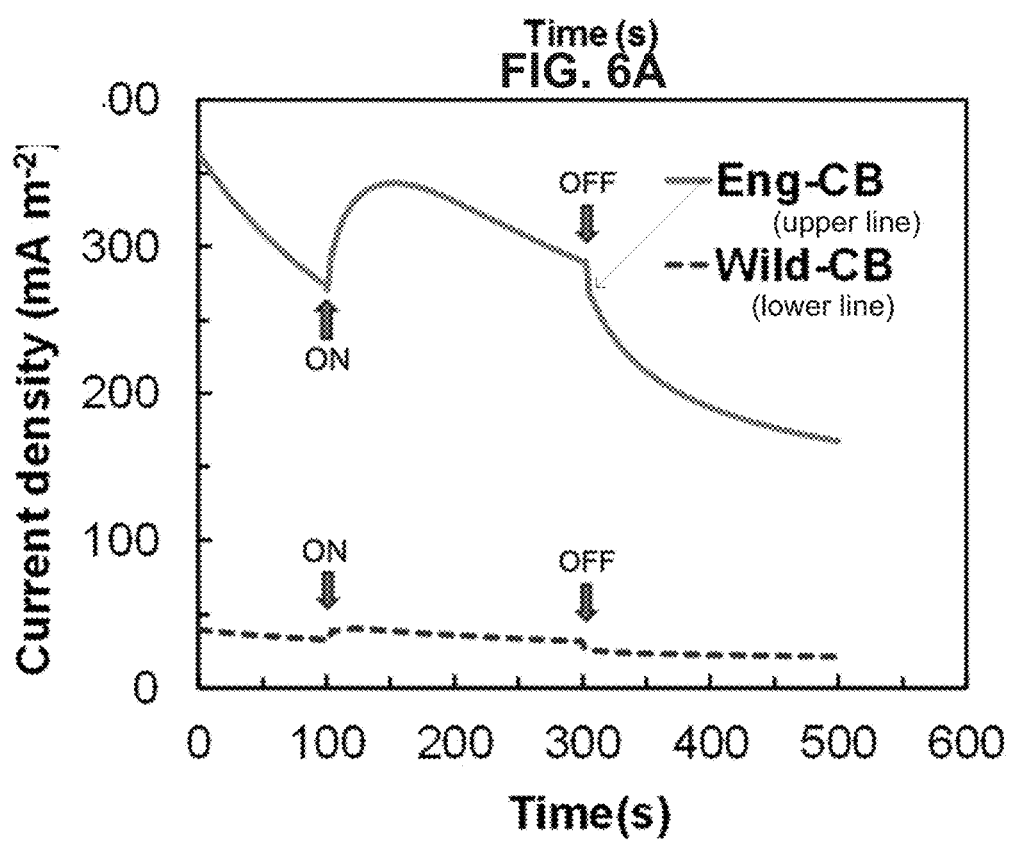
Figure 7:
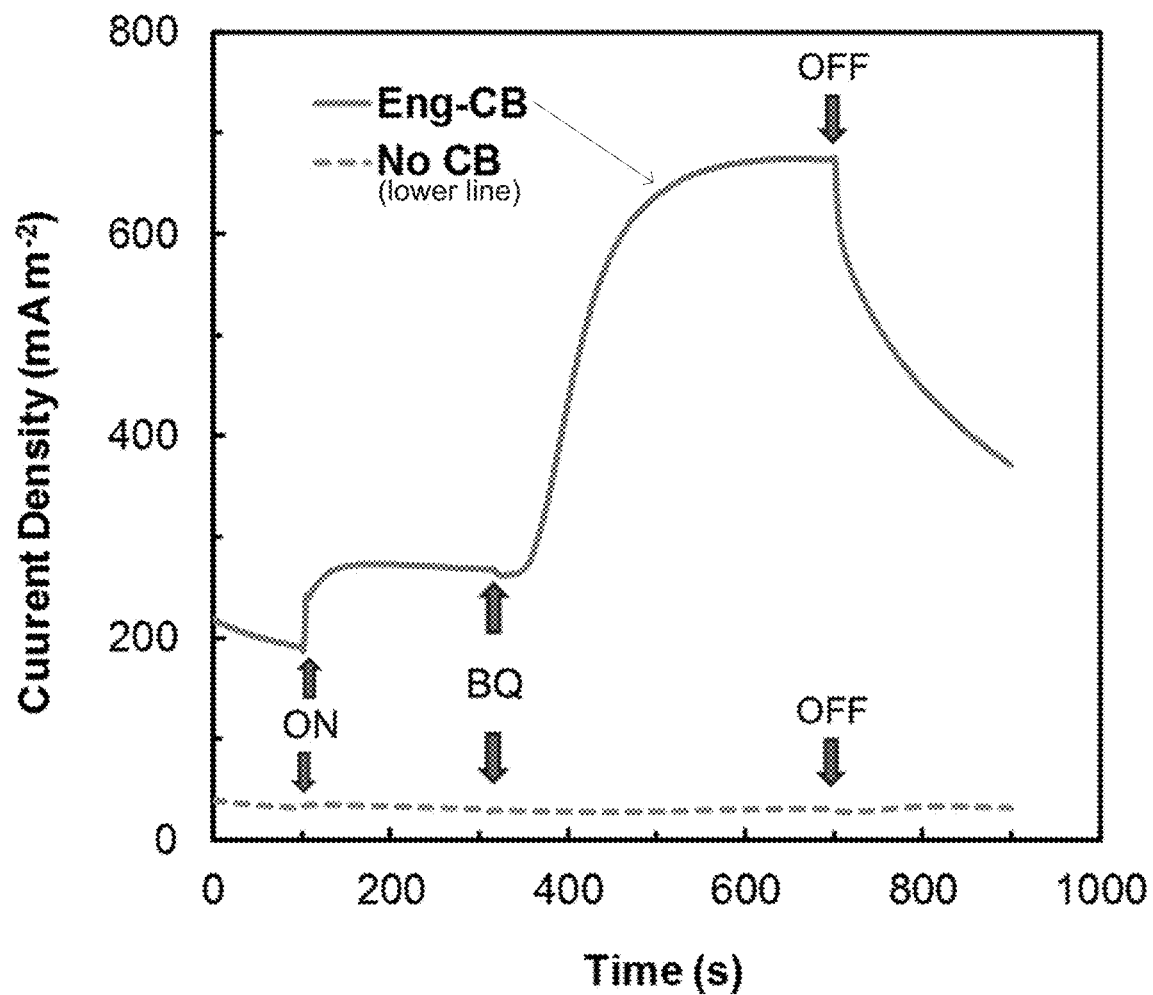
FIG. 7 illustrates mediated electron transfer exhibited by Eng-CB using 1,4-benzoquinone (BQ) as redox mediator. Upon addition of BQ (1 μM) during light phase, Eng-CB generated a higher current compared to the direct electron transfer.

The current generated by Eng-CB and Wild-CB was measured by applying over-potential of 0.1 V (vs. Ag/AgCl) for both (0.2 V for Eng-CB and 0.25 V for Wild-CB). Eng-CB was observed to generate ~9 fold higher current compared to Wild-CB as shown in FIG. 6B. In addition to the enhanced DET shown by Eng-CB, its mediated electron transfer ability was also evaluated using 1,4-benzoquinone (1 µM) as a redox mediator as shown in FIG. 7. 1,4-benzoquinone mimics the plastoquinone naturally present in the PETC and has been demonstrated to enhance mediated EET. Increase in current was found by adding 1,4-benzoquinone as mediator in the presence of light (FIG. 7). Taken together, both the biochemical reduction of potassium ferricyanide and the electrochemical measurement of photocurrent confirmed that the heterogeneously expressed omcS enhanced the direct extracellular electron transfer ability of *S. elongatus*.

In *Geobacter* sp., OmcS is a predominant terminal cytochrome that transfers electron from cytochrome bc complex in cytoplasmic membrane to the external milieu with the help of other intermediate periplasmic c-type cytochromes such as MacA and PpcA. Both the cytochrome bc complex of *G. sulfurreducens* and cytochromes $b_6 f$ complex (Cyt $b_6 f$) of *S. elongatus* are functionally related and belong to the highly conserved Rieske/cytochromes b complexes. Further, certain c-type cytochromes such as cytochromes $c_6$ (Cyt $c_6$) are also found in periplasmic space of cyanobacteria that might have functionally complemented the activity of MacA and PpcA.

Figure 5B:
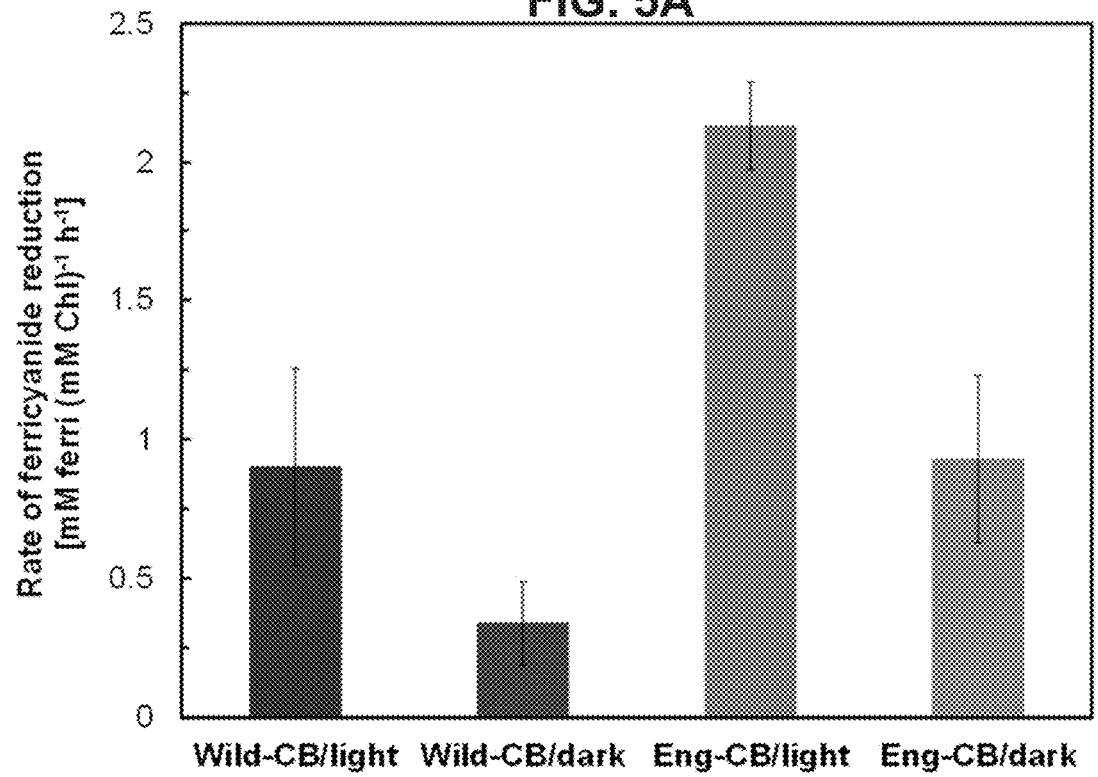
FIG. 5B is a bar graph illustrating ferricyanide reduction (normalized with the average chlorophyll content) of Wild-CB and Eng-CB calculated using the raw data in FIG. 5A over the first 12 hours in both light and dark conditions. Each data point/bar shown is average of three independent experiments with SD as error bars. Eng-CB exhibited ~2 fold higher rate of ferricyanide reduction in light and ~2.5 fold higher in dark compared to the Wild-CB under the same conditions.
Figure 8:
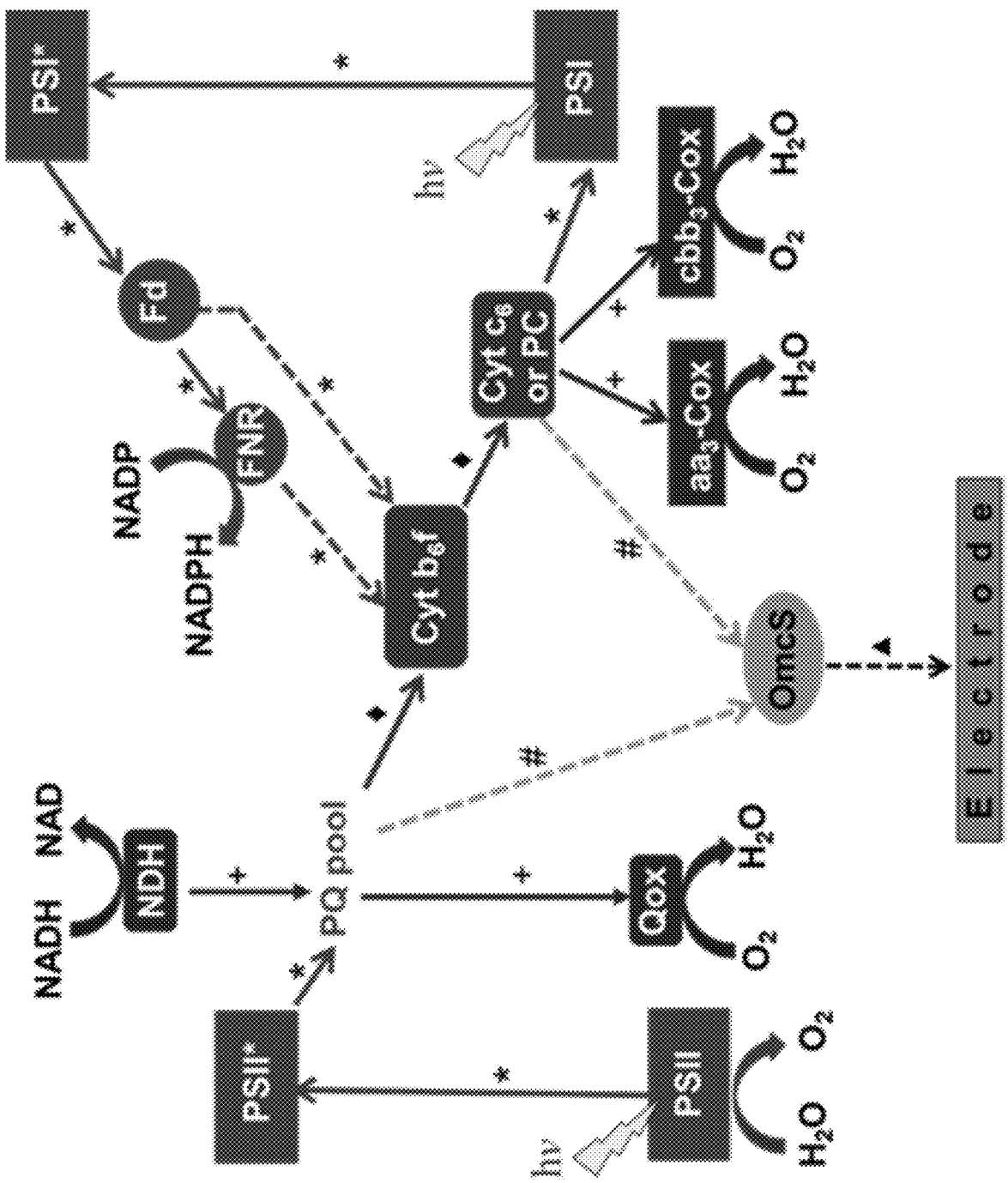
FIG. 8 is a schematic illustrating the electron transfer pathways from photosynthetic (P-ETC) and respiratory electron transport chain (R-ETC) to OmcS. * solid arrows: P-ETC; * broken arrows: cyclic P-ETC; + solid arrows: R-ETC; ♦ solid arrows: pathway shared by both P-ETC and R-ETC; # broken arrows: hypothesized electron transfer pathways to OmcS; ▲ broken arrows: extracellular electron transfer to the electrode; (PSII: photosystem II; PSII*: excited photosystem II; PQ pool: plastoquinone pool; Cyt $b_6f$: cytochrome $b_6f$ complex; PC: plastocyanin; Cyt $C_6$: cytochrome $c_6$; PSI: photosystem I; PSI*: excited photosystem I; Fd: ferredoxin; FNR: ferredoxin NADP reductase; NDH: NADH dehydrogenase; Qox: bd-type quinol oxidase; $aa_3$-Cox: $aa_3$-type cytochrome c oxidase; $cbb_3$-Cox: $cbb_3$-type cytochrome c oxidase).

Thus, it is believed that electrons from Cyt $b_6 f$ were transferred to OmcS through Cyt $c_6$ (FIG. 8). Further, Cyt $b_6 f$ is involved in both PETC and RETC, which appropriately correlated with the observation that the OmcS enhanced EET under both light and dark conditions as shown in FIG. 5B. It is noteworthy that, in addition to Cyt $b_6 f$ and Cyt $c_6$, plastoquinones are also shared between both PETC and RETC. When the photosystems absorb more light than that can be handled by PETC, the more reduced plastoquinone pool buffers the PETC by channelling the excess electrons to respiratory terminal oxidases such as bd-type quinol oxidase (Qox) and alternate respiratory terminal oxidase (ARTO). It is likely that this overflow mechanism by plastoquinones might have extended to the OmcS, leading to more EET (FIG. 8) in Eng-CB.

Conclusions

*S. elongatus* was genetically engineered to express heterologous OmcS, and expression of the active OmcS was confirmed. Eng-CB was found to exhibit enhanced extracellular electron transfer as evident from both the higher rate of ferricyanide reduction (~2 fold) and higher photocurrent generation (~9 fold) compared to the wild-type cyanobacterium. The higher rate of ferricyanide reduction under both light and dark conditions by Eng-CB underlines the fact that OmcS interacted with both photosynthetic and respiratory electron transport chain of cyanobacteria.

Example 3

Cyclic voltammogram techniques, with a scan rate as low as 1 mV/s, has been used in microbial fuel cells to probe the electrochemistry of redox proteins on bacterial outer membrane that are in direct contact with the electrode (as described in Baron, D., et al. (2009). "Electrochemical Measurement of Electron Transfer Kinetics by *Shewanella oneidensis* MR-1." *Journal of Biological Chemistry* 284 (42): 28865-28873 and Carmona-Martinez, A. A., et al. (2013). "Electron transfer and biofilm formation of *Shewanella putrefaciens* as function of anode potential." *Bioelectrochemistry* 93: 23-29, both of which are incorporated by reference herein). In the present example, a similar procedure was conducted to characterize the Eng-CB (made as described in Example 2, above).

Experimental Procedure

Eng-CB cells were made as described in Example 2, above. A three electrode system was set up, using Eng-CB immobilized on multi-walled carbon nanotubes (CNT) modified glassy carbon electrode, as a working electrode, Ag/AgCl (sat. KCl) as a reference electrode, and platinum wire as a counter electrode. CV was performed by sweeping the potential between –0.2 V (vs Ag/AgCl) and 0.8 V (vs Ag/AgCl) at a scan rate of 1 mV/s.

Results and Discussion

Figure 9:
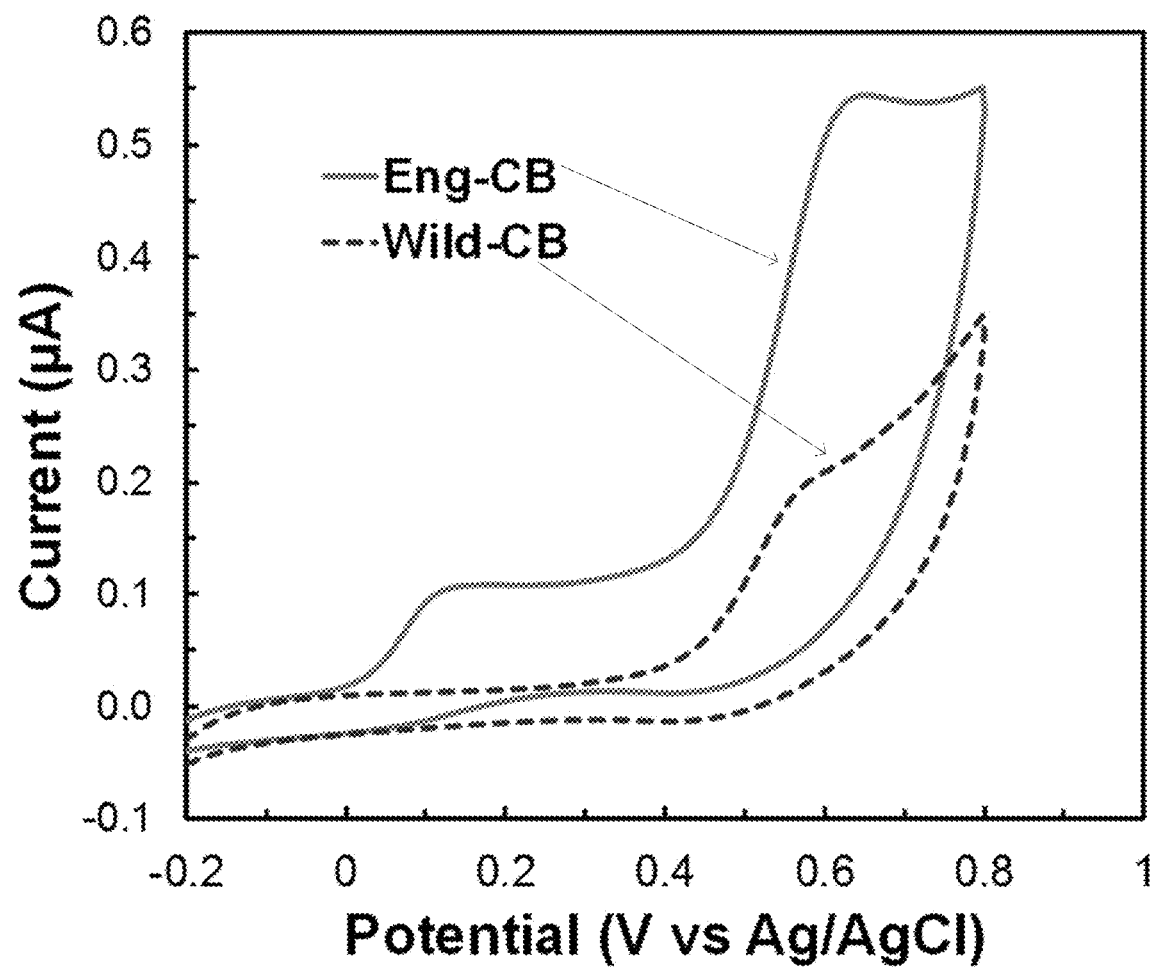
FIG. 9 illustrates cyclic voltammograms showing the enhanced direct electron transfer by Eng-CB compared with that by Wild-CB; Scan rate: 1 mV/s.

The cyclic voltammograms of the Eng-CB vs. the Wild-CB are shown in FIG. 9. The Eng-CB exhibited a specific oxidation peak at 0.1 V (vs. Ag/AgCl), and the same was not observed in the Wild-CB. This redox peak corresponds to the heterologously expressed outer membrane cytochrome OmcS, which is responsible for the enhanced photo-electrochemical activity of Eng-CB as witnessed in ferricyanide reduction (FIG. 5) and photocurrent generation (FIG. 6B), described in Example 2, above.

Example 4

This example describes another embodiment of a photo-bioelectrochemical cell incorporating an engineered photosynthetic CB of the present disclosure on the anode and a cathode modified with CNT and laccase. The photo-bioelectrochemical cell is a self-sustainable system using only water and light as fuel without the necessity for any external organic carbon source. CB on the anode do photosynthesis in the presence of light and transfer electrons from the P-ETC to the electrode. The oxygen generated as the by-product of photosynthesis is enzymatically reduced at the cathode to form water (FIG. 10a).

Experimental Procedure

Figure 10A:
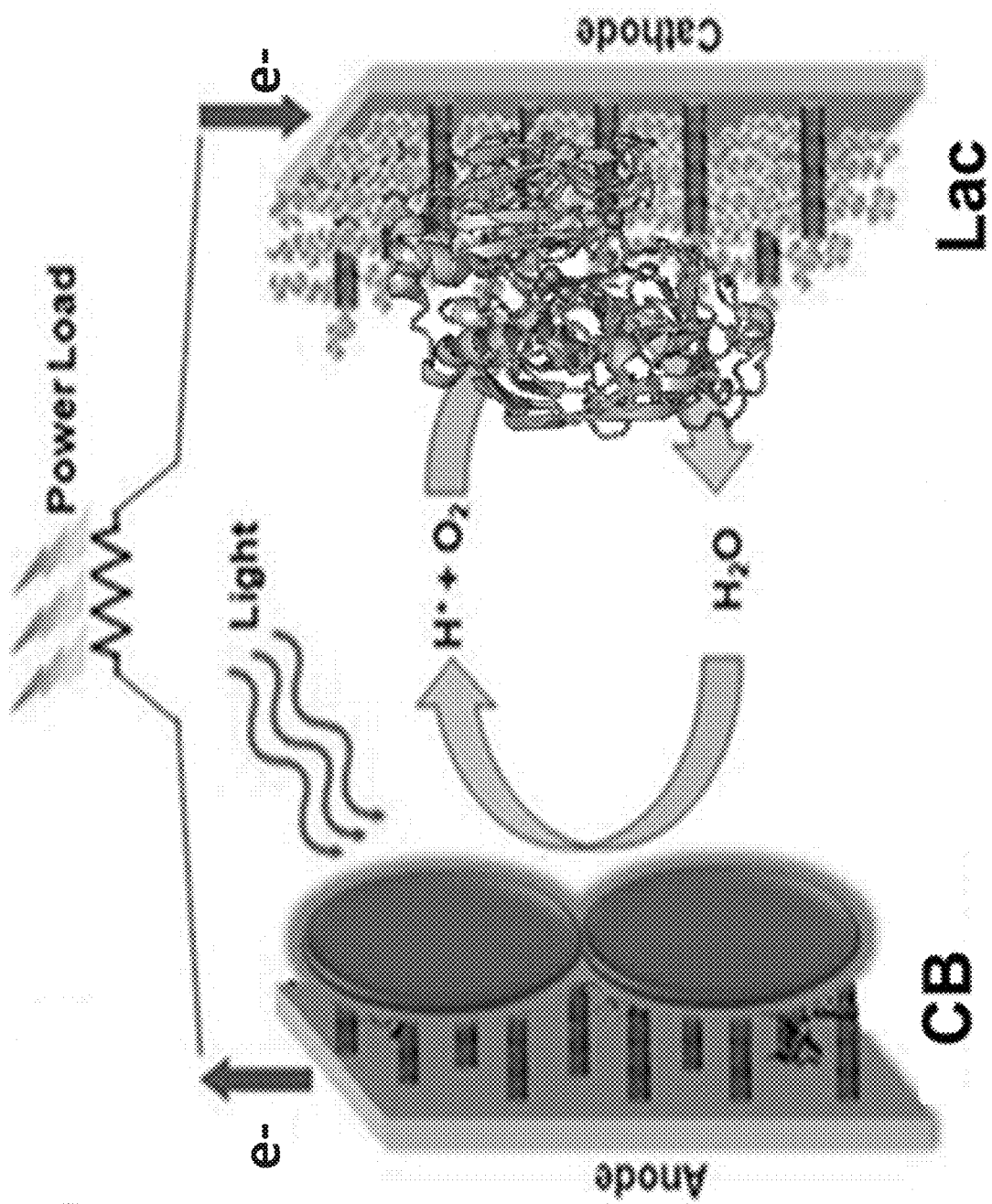
FIG. 10A is a schematic illustrating power generation in an embodiment of a photo-bioelectrochemical full cell of the present disclosure with engineered cyanobacteria (CB) immobilized anode and laccase based bio-cathode.

The photo-bioelectrochemical full cell was developed using CP/CNT/WT-CB or CP/CNT/Eng-CB as anode and CP/CNT/laccase as the enzymatic cathode as shown in FIG. 10A. The anodes were made as described in Examples 2 and 3 above. For the cathode, a molecular tethering approach using PBSE (1-pyrenebutanoic acid, succinimidyl ester) was used to immobilize laccase onto CNT modified electrode. Potassium phosphate buffer (100 mM, pH 5.8) was used as the electrolyte in the full cell. A Dolan-Jenner Industries Fibre-Lite lamp (model 190: quartz-halogen vibration less light source, 3100 K color temperature) with a light intensity of 76 mW/cm$^2$ was used for illumination.

Results and Discussion

Figure 10B:
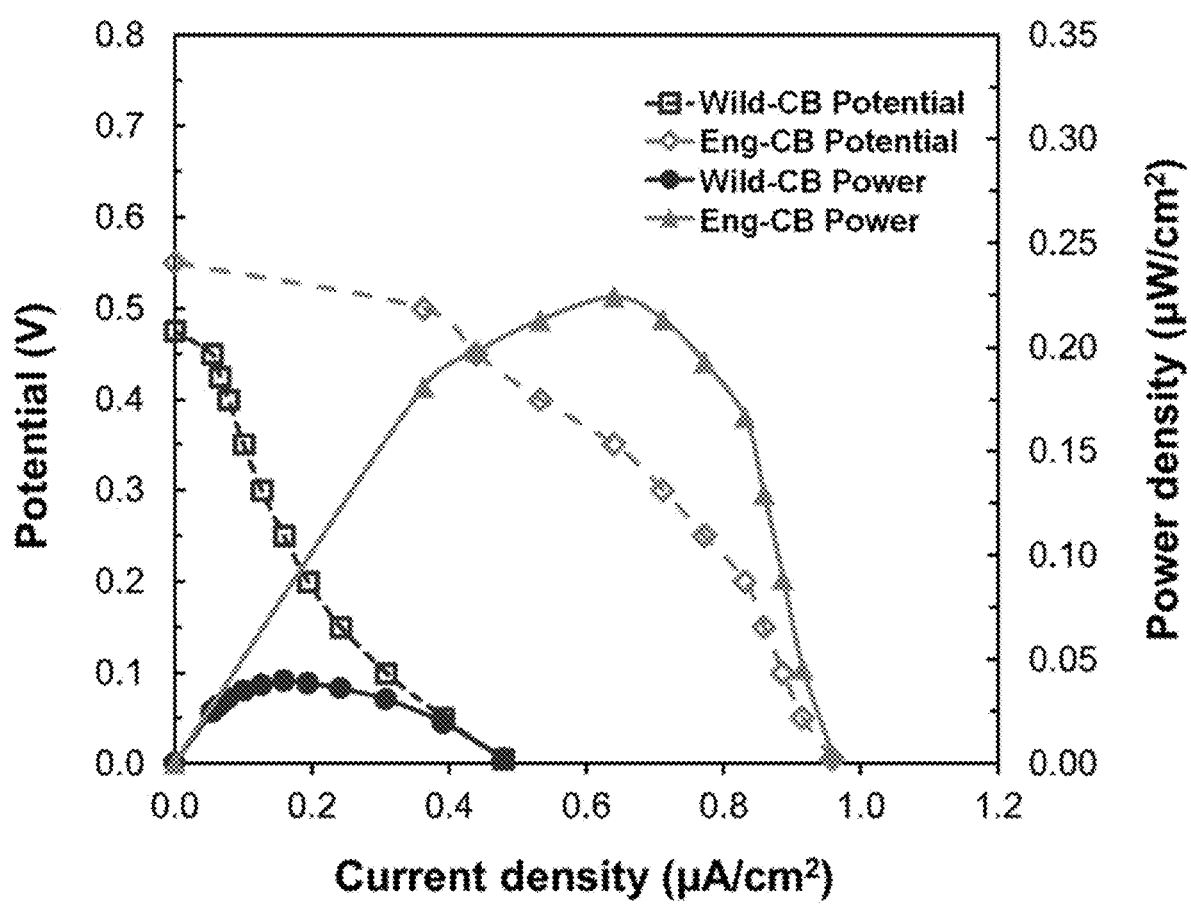
FIG. 10B is a graph illustrating polarization and power density curves of a photo-bioelectrochemical full cell with anode: CP/CNT/Wild-CB or CP/CNT/Eng-CB and a laccase based biocathode: Carbon/CNT/laccase.

FIG. 10B shows the current density and the power density generated by WT-CB and Eng-CB in the full cell. The polarization curve was generated by measuring the current at different applied potential. Power density was calculated by multiplying the potential with the current density. It is evident that peak power density generated by Eng-CB (0.22 µW/cm$^2$) is nearly five times higher than that generated by WT-CB (0.04 µW/cm$^2$). The maximum current density generated by Eng-CB (1 µA/cm$^2$) is twice as that generated by the WT-CB (0.5 µA/cm$^2$). These data demonstrate that the Eng-CB performed better than the WT-CB in photocurrent generation due to the heterologous expression of outer membrane cytochrome OmcS. However, engineering optimizations such as better cell design, usage of three dimensional brush electrodes, etc., could result in much higher power densities than that reported here.

PEPTIDE AND NUCLEIC ACID SEQUENCES

SEQ ID NO: 1 OmcS forward primer
GGGAAAGAATTCGAAGGAGTATACCTATACATGAAGAAAGGCATGAAAGT

TAGTCTGA

SEQ ID NO: 2 OmcS reverse primer
GGGAAAGGATCCTTAATCTTTGGCGTGGCATTTGTTAC

SEQ ID NO: 3: nucleotide sequence for codon
optimized OmcS coding sequence, 1299 bp
ATGAAGAAAGGCATGAAAGTTAGTCTGAGCGTGGCGGCGGCAGCACTCCT

GATGTCGGCACCGGCAGCGTTCGCATTCCATTCGGGCGGCGTGGCTGAAT

GCGAGGGTTGTCACACCATGCATAACAGCCTCGGTGGTGCAGTCATGAAC

AGCGCAACGGCACAGTTCACCACGGGTCCAATGCTGCTCCAGGGTGCAAC

CCAAAGCTCGAGTTGCCTGAACTGTCACCAACATGCGGGCGATACGGGTC

CCAGCTCGTACCACATCAGCACTGCTGAAGCAGACATGCCCGCTGGCACC

GCACCGTTGCAGATGACGCCTGGCGGTGATTTTGGCTGGGTCAAAAAGAC

CTATACGTGGAACGTTCGCGGCCTGAATACGAGCGAAGGCGAGCGCAAAG

GTCACAACATTGTTGCGGGCGATTACAATTATGTGGCTGACACTACCCTC

ACGACTGCACCAGGTGGCACCTACCCAGCAAACCAGTTGCATTGCAGTAG

CTGTCACGATCCGCATGGCAAATATCGCCGCTTCGTCGACGGCTCGATCG

CAACCACGGGTCTGCCGATTAAGAATAGCGGCTCGTACCAAAACAGCAAT

GATCCTACGGCATGGGGTGCAGTTGGTGCTTACCGCATCCTCGGTGGCAC

CGGCTATCAGCCTAAAAGTTTGAGCGGTTCGTATGCCTTTGCAAACCAAG

TGCCGGCAGCAGTCGCACCTAGCACCTACAATCGCACGGAAGCGACTACC

CAGACCCGCGTGGCTTATGGCCAGGGTATGAGTGAGTGGTGCGCGAATTG

TCACACCGATATCCATAACAGCGCTTACCCAACGAATCTGCGCCACCCAG

CCGGTAACGGTGCTAAGTTCGGTGCAACCATTGCCGGTCTGTACAATTCG

TATAAAAAGAGTGGCGATCTCACTGGCACCCAGGCTAGCGCATACTTGTC

GCTGGCACCGTTTGAAGAGGGCACTGCCGATTATACCGTTTTGAAAGGTC

ATGCAAAGATTGATGACACGGCACTGACTGGTGCAGACGCAACGTCGAAC

GTGAATTGCCTGAGTTGTCACCGCGCTCATGCAAGTGGCTTTGATAGCAT

GACCCGCTTCAACCTCGCCTACGAATTTACGACTATCGCCGATGCGAGTG

GCAACAGCATTTATGGTACGGACCCCAATACTTCGAGTCTGCAAGGCCGC

AGCGTCAATGAGATGACTGCTGCATACTATGGCCGCACCGCAGACAAGTT

CGCACCCTACCAACGCGCCCTGTGTAACAAATGCCACGCCAAAGATTAA

SEQ ID NO: 4: peptide sequence for OmcS encoded by
SEQ ID NO: 3
MKKGMKVSLSVAAAALLMSAPAAFAFHSGGVAECEGCHTMHNSLGGAVMN

SATAQFTTGPMLLQGATQSSSCLNCHQHAGDTCPSSYHISTAEADMPAGT

APLQMTPGGDFGWVKKTYTWNVRGLNTSEGERKGHNIVAGDYNYVADTTL

TTAPGGTYPANQLHCSSCHDPHGKYRRFVDGSIATTGLPIKNSGSYQNSN

DPTAWGAVGAYRILGGTGYQPKSLSGSYAFANQVPAAVAPSTYNRTEATT

QTRVAYGQGMSEWCANCHTDIHNSAYPTNLRHPAGNGAKFGATIAGLYNS

YKKSGDLTGTQASAYLSLAPFEEGTADYTVLKGHAKIDDTALTGADATSN

VNCLSCHRAHASGFDSMTRFNLAYEFTTIADASGNSIYGTDPNTSSLQGR

SVNEMTAAYYGRTADKFAPYQRALCNKCHAKD

REFERENCES

J. M. Pisciotta, Y. Zou and I. V. Baskakov, *Plos One*, 2010, 5.

N. Sekar, Y. Umasankar and R. P. Ramasamy, *Physical Chemistry Chemical Physics*, 2014, 16, 7862-7871.

B. E. Logan, *Nature Reviews Microbiology*, 2009, 7, 375-381.

Y. Yang, M. Xu, J. Guo and G. Sun, *Process Biochemistry*, 2012, 47, 1707-1714.

D. R. Lovley, *Current Opinion in Biotechnology*, 2008, 19, 564-571.

T. Mehta, M. V. Coppi, S. E. Childers and D. R. Lovley, *Applied and Environmental Microbiology*, 2005, 71, 8634-8641.

X. Qian, T. Mester, L. Morgado, T. Arakawa, M. L. Sharma, K. Inoue, C. Joseph, C. A. Salgueiro, M. J. Maroney and D. R. Lovley, *Biochimica Et Biophysica Acta-Bioenergetics*, 2011, 1807, 404-412.

C. Leang, X. Qian, T. Mester and D. R. Lovley, *Applied and Environmental Microbiology*, 2010, 76, 4080-4084.

R. E. Blankenship, D. M. Tiede, J. Barber, G. W. Brudvig, G. Fleming, M. Ghirardi, M. R. Gunner, W. Junge, D. M. Kramer, A. Melis, T. A. Moore, C. C. Moser, D. G. Nocera, A. J. Nozik, D. R. Ort, W. W. Parson, R. C. Prince and R. T. Sayre, *Science*, 2011, 332, 805-809.

N. B. Ivleva, M. R. Bramlett, P. A. Lindahl and S. S. Golden, *Embo Journal*, 2005, 24, 1202-1210.

P. E. Thomas, D. Ryan and W. Levin, *Analytical Biochemistry*, 1976, 75, 168-176.

R. W. Bradley, P. Bombelli, D. J. Lea-Smith and C. J. Howe, *Physical Chemistry Chemical Physics*, 2013, 15, 13611-13618.

Shestako. Sv and N. T. Khyen, *Molecular and General Genetics*, 1970, 107, 372-&.

T. Yagishita, T. Horigome and K. Tanaka, *Journal of Chemical Technology and Biotechnology*, 1993, 56, 393-399.

S. Tsujimura, A. Wadano, K. Kano and T. Ikeda, *Enzyme and Microbial Technology*, 2001, 29, 225-231.

J. E. Butler, F. Kaufmann, M. V. Coppi, C. Nunez and D. R. Lovley, *Journal of Bacteriology*, 2004, 186, 4042-4045.

J. R. Lloyd, C. Leang, A. L. H. Myerson, M. V. Coppi, S. Cuifo, B. Methe, S. J. Sandler and D. R. Lovley, *Biochemical Journal*, 2003, 369, 153-161.

J. L. Cape, M. K. Bowman and D. M. Kramer, *Trends in Plant Science*, 2006, 11, 46-55.

C. Obinger, J. C. Knepper, U. Zimmermann and G. A. Peschek, *Biochemical and Biophysical Research Communications*, 1990, 169, 492-501.

W. F. J. Vermaas, *Photosynthesis and Respiration in Cyanobacteria*, Macmillan Publishers Ltd, Nature Publishing Group, 2001.

J. M. Pisciotta, Y. Zou and I. V. Baskakov, *Applied Microbiology and Biotechnology*, 2011, 91, 377-385.

Baron, D., et al. (2009). "Electrochemical Measurement of Electron Transfer Kinetics by *Shewanella oneidensis* MR-1." *Journal of Biological Chemistry* 284 (42): 28865-28873.

Carmona-Martinez, A. A., et al. (2013). "Electron transfer and biofilm formation of *Shewanella putrefaciens* as function of anode potential." *Bioelectrochemistry* 93: 23-29.

Inoue, K., et al. (2010). "Purification and Characterization of OmcZ, an Outer-Surface, Octaheme c-Type Cytochrome Essential for Optimal Current Production by *Geobacter sulfurreducens*." *Applied and Environmental Microbiology* 76 (12): 3999-4007.

Jeamton, W., et al. (2011). "Phycocyanin promoter of Spirulina platensis controlling heterologous expression in cyanobacteria." *Journal of Applied Phycology* 23 (1): 83-88.

Leang, C., et al. (2003). "OmcB, a c-type polyheme cytochrome, involved in Fe(III) reduction in *Geobacter sulfurreducens*." *Journal of Bacteriology* 185 (7): 2096-2103.

Nair, U., et al. (2001). "Functional elements of the strong psbAI promoter of *Synechococcus elongatus* PCC 7942." *Journal of Bacteriology* 183 (5): 1740-1747.

Stevens, S. E. and R. D. Porter (1980). "TRANSFORMATION IN AGMENELLUM-QUADRUPLICATUM." *Proceedings of the National Academy of Sciences of the United States of America—Biological Sciences* 77 (10): 6052-6056.

GeneArt *Synechococcus* Engineering Kits by Invitrogen life technologies USER GUIDE Publication number MAN0005339

N. Sekar, R. Jain, Y. Yan and R. P. Ramasamy, *Biotechnology Bioengineering*, 2016, 113 (3): 675-679.

We claim:

1. An anode for a photo-bioelectrochemical cell (PBEC) or a photosynthetic microbial fuel cell (PMFC) comprising:
an anode material;
a matrix of nanostructured material; and
one or more engineered photosynthetic cyanobacterium, each engineered photosynthetic cyanobacterium comprising:
an exogenous nucleic acid molecule encoding a non-native, multi-heme, outer membrane cytochrome (Omc) from an exoelectrogenic organism and capable of extracellular electron transport, and
a promoter operatively linked to the exogenous nucleic acid molecule encoding the Omc, such that the Omc is expressed in the engineered photosynthetic cyanobacterium, wherein the engineered photosynthetic cyanobacterium has increased extracellular electron transport compared to a corresponding wild-type cyanobacterium that does not comprise the exogenous nucleic acid molecule encoding the Omc,
wherein the anode is configured such that the matrix of nanostructured material is in electrochemical communication with the engineered photosynthetic cyanobacterium and couples the photosynthetic cyanobacterium to the anode material, such that when the engineered photosynthetic cyanobacterium oxidizes water molecules and generates electrons using a light induced photo-electrochemical reaction, at least a portion of electrons generated by the photosynthetic cyanobacterium are transferred to the anode material via direct electron transfer.

2. The anode of claim 1, wherein the matrix of nanostructured materials is selected from the group of nanostructured materials consisting of: carbon nanotubes, multi-walled carbon nanotubes, fullerenes, carbon nanoparticles, graphenes, two-dimensional carbon nanosheets, graphite platelets, other carbon nanostructured materials, metallic nanoparticles, semiconductor nanoparticles, quantum dots and combinations of these materials.

3. The anode of claim 1, wherein the engineered photosynthetic cyanobacterium is coupled to the nanostructured material by a linking agent.

4. The anode of claim 3, wherein the linking agent is selected from the group of linking agents consisting of: 1-pyrenebutanoic acid succinimidyl ester (PBSE), a protein homo-bifunctional cross-linking agent, a hetero-bifunctional cross-linking agent, and combinations thereof.

5. The anode of claim 1, wherein the cyanobacterium is selected from the group of cyanobacterium consisting of: *Synechococcus elongatus* PCC 7942 and *Synechocystis* sp. PCC6803.

6. The anode of claim 1, wherein the exoelectrogenic organism is a microorganism selected from a genus *Geobacter* or *Shewanella*.

7. The anode of claim 1, wherein the Omc is from *Geobacter sulfurreducens*.

8. The anode of claim 1, wherein the nucleic acid encoding the Omc has a nucleic acid sequence having at least 75% sequence identity with SEQ ID NO: 3 and encoding an Omc having the capability of extracellular electron transport.

9. The anode of claim 1, wherein the Omc is outer membrane cytochrome S (OmcS) from *Geobacter sulfurreducens*.

10. The anode of claim 9, wherein the exogenous nucleic acid molecule encoding the outer membrane cytochrome S (OmcS) from *Geobacter sulfurreducens* comprises SEQ ID NO: 3.

11. The anode of claim 1, further comprising one or more exogenous nucleic acid molecules encoding one or more intermediate cytochromes capable of electron transfer to the Omc, wherein the one or more intermediate cytochromes are selected from the group consisting of: outer membrane cytochrome B (OmcB), MacA, and PpcA from *Geobacter sulfurreducens*, MtrABC and OmcA from *Shewanella* sp.

12. A photo-bioelectrochemical cell (PBEC) or a photosynthetic microbial fuel cell (PMFC) comprising:
   the anode of claim 1; and
   a cathode composite comprising a cathode material and at least one enzyme or metallic catalyst capable of reducing a reductant.

13. A PBEC of claim 12, wherein the at least one enzyme or metallic catalyst is capable of reducing $O_2$.

14. The PBEC of claim 13, wherein the at least one enzyme or metallic catalyst capable of reducing $O_2$ is an enzyme selected from the group consisting of: laccase, bilirubin oxidase, ascorbate oxidase, tyrosinase, catechol oxidase, and combinations thereof.

15. A PMFC of claim 12, wherein the at least one enzyme or metallic catalyst is capable of reducing $H^+$ to produce $H_2$.

16. The PBEC or PMFC of claim 12, further comprising a redox mediator.

17. The PBEC or PMFC of claim 12, wherein the anode material and cathode composite are selected from the group of materials consisting of: carbon, metal, semiconductor, and combinations thereof, wherein the conducting materials are in bulk form, nanostructure form, or a combination thereof.

18. The PBEC or PMFC of claim 12, wherein the cathode composite further comprises a matrix of nanostructured material coupling the cathode material to the at least one enzyme or metallic catalyst capable of reducing the reductant.

19. A method of generating an electrical current or generating $H_2$ fuel, the method comprising:
   providing a photo-bioelectrochemical cell (PBEC) or photosynthetic microbial fuel cell (PMFC) of claim 12, wherein the reductant at the cathode is $O_2$ or $H^+$, and
   exposing the PBEC/PMFC to light in the presence of water, wherein the engineered photosynthetic cell(s) or organism(s) uses light energy to oxidize a water molecule and generate electrons, which are transferred to the anode via the nanostructured material, and wherein the electrons reduce $O_2$ at the cathode, thereby inducing a potential difference between the anode and the cathode and generating an electrical current, or wherein the electrons reduce $H^+$ at the cathode, thereby generating $H_2$.

* * * * *

SEQUENCE LISTING

```
<160> NUMBER OF SEQ ID NOS: 4

<210> SEQ ID NO 1
<211> LENGTH: 58
<212> TYPE: DNA
<213> ORGANISM: Artificial Sequence
<220> FEATURE:
<223> OTHER INFORMATION: Chemically synthesized OmcS forward primer

<400> SEQUENCE: 1
gggaaagaat tcgaaggagt atacctatac atgaagaaag gcatgaaagt tagtctga        58

<210> SEQ ID NO 2
<211> LENGTH: 38
<212> TYPE: DNA
<213> ORGANISM: Artificial Sequence
<220> FEATURE:
<223> OTHER INFORMATION: chemically synthesized OmcS reverse primer

<400> SEQUENCE: 2
gggaaaggat ccttaatctt tggcgtggca tttgttac                              38

<210> SEQ ID NO 3
<211> LENGTH: 1299
<212> TYPE: DNA
<213> ORGANISM: Artificial Sequence
<220> FEATURE:
<223> OTHER INFORMATION: chemically synthesized nucleotide sequence for
      codon optimized OmcS coding sequence

<400> SEQUENCE: 3
atgaagaaag gcatgaaagt tagtctgagc gtggcggcgg cagcactcct gatgtcggca      60
ccggcagcgt tcgcattcca ttcgggcggc gtggctgaat gcgagggttg tcacaccatg     120
cataacagcc tcggtggtgc agtcatgaac agcgcaacgg cacagttcac cacgggtcca     180
atgctgctcc agggtgcaac ccaaagctcg agttgcctga actgtcacca acatgcgggc     240
gatacgggtc ccagctcgta ccacatcagc actgctgaag cagacatgcc cgctggcacc     300
gcaccgttgc agatgacgcc tggcggtgat tttggctggg tcaaaaagac ctatacgtgg     360
aacgttcgcg gcctgaatac gagcgaaggc gagcgcaaag gtcacaacat tgttgcgggc     420
gattacaatt atgtggctga cactaccctc acgactgcac caggtggcac ctacccagca     480
aaccagttgc attgcagtag ctgtcacgat ccgcatggca aatatcgccg cttcgtcgac     540
ggctcgatcg caaccacggg tctgccgatt aagaatagcg gctcgtacca aaacagcaat     600
```

-continued

```
gatcctacgg catggggtgc agttggtgct taccgcatcc tcggtggcac cggctatcag    660
cctaaaagtt tgagcggttc gtatgccttt gcaaaccaag tgccggcagc agtcgcacct    720
agcacctaca atcgcacgga agcgactacc cagacccgcg tggcttatgg ccagggtatg    780
agtgagtggt gcgcgaattg tcacaccgat atccataaca gcgcttaccc aacgaatctg    840
cgccacccag ccggtaacgg tgctaagttc ggtgcaacca ttgccggtct gtacaattcg    900
tataaaaaga gtggcgatct cactggcacc caggctagcg catacttgtc gctggcaccg    960
tttgaagagg gcactgccga ttataccgtt ttgaaaggtc atgcaaagat tgatgacacg   1020
gcactgactg gtgcagacgc aacgtcgaac gtgaattgcc tgagttgtca ccgcgctcat   1080
gcaagtggct ttgatagcat gacccgcttc aacctcgcct acgaatttac gactatcgcc   1140
gatgcgagtg caacagcat ttatggtacg acccccaata cttcgagtct gcaaggccgc    1200
agcgtcaatg agatgactgc tgcatactat ggccgcaccg cagacaagtt cgcaccctac   1260
caacgcgccc tgtgtaacaa atgccacgcc aaagattaa                          1299
```

<210> SEQ ID NO 4
<211> LENGTH: 420
<212> TYPE: PRT
<213> ORGANISM: Artificial Sequence
<220> FEATURE:
<223> OTHER INFORMATION: chemically synthesized protein sequence for OmcS enzyme

<400> SEQUENCE: 4

```
Met Lys Lys Gly Met Lys Val Ser Leu Ser Val Ala Ala Ala Ala Leu
1               5                   10                  15

Leu Met Ser Ala Pro Ala Ala Phe Ala Phe His Ser Gly Gly Val Ala
                20                  25                  30

Glu Cys Glu Gly Cys His Thr Met His Asn Ser Leu Gly Gly Ala Val
            35                  40                  45

Met Asn Ser Ala Thr Ala Gln Phe Thr Thr Gly Pro Met Leu Leu Gln
        50                  55                  60

Gly Ala Thr Gln Ser Ser Ser Cys Leu Asn Cys His Gln His Ala Gly
65                  70                  75                  80

Asp Thr Gly Pro Ser Ser Tyr His Ile Ser Thr Ala Glu Ala Asp Met
                85                  90                  95

Pro Ala Gly Thr Ala Pro Leu Gln Met Thr Pro Gly Gly Asp Phe Gly
            100                 105                 110

Trp Val Lys Lys Thr Tyr Thr Trp Asn Val Arg Gly Leu Asn Thr Ser
        115                 120                 125

Glu Gly Glu Arg Lys Gly His Asn Ile Val Ala Gly Asp Tyr Asn Tyr
    130                 135                 140

Val Ala Asp Thr Thr Leu Thr Thr Ala Pro Gly Gly Tyr Pro Ala
145                 150                 155                 160

Asn Gln Leu His Cys Ser Ser Cys His Asp Pro His Gly Lys Tyr Arg
                165                 170                 175

Arg Phe Val Asp Gly Ser Ile Ala Thr Thr Gly Leu Pro Ile Lys Asn
            180                 185                 190

Ser Gly Ser Tyr Gln Asn Ser Asn Asp Pro Thr Ala Trp Gly Ala Val
        195                 200                 205

Gly Ala Tyr Arg Ile Leu Gly Gly Thr Gly Tyr Gln Pro Lys Ser Leu
    210                 215                 220

Ser Gly Ser Tyr Ala Phe Ala Asn Gln Val Pro Ala Ala Val Ala Pro
225                 230                 235                 240
```

```
Ser Thr Tyr Asn Arg Thr Glu Ala Thr Thr Gln Thr Arg Val Ala Tyr
                245                 250                 255
Gly Gln Gly Met Ser Glu Trp Cys Ala Asn Cys His Thr Asp Ile His
            260                 265                 270
Asn Ser Ala Tyr Pro Thr Asn Leu Arg His Pro Ala Gly Asn Gly Ala
        275                 280                 285
Lys Phe Gly Ala Thr Ile Ala Gly Leu Tyr Asn Ser Tyr Lys Lys Ser
    290                 295                 300
Gly Asp Leu Thr Gly Thr Gln Ala Ser Ala Tyr Leu Ser Leu Ala Pro
305                 310                 315                 320
Phe Glu Glu Gly Thr Ala Asp Tyr Thr Val Leu Lys Gly His Ala Lys
                325                 330                 335
Ile Asp Asp Thr Ala Leu Thr Gly Ala Asp Ala Thr Ser Asn Val Asn
            340                 345                 350
Cys Leu Ser Cys His Arg Ala His Ala Ser Gly Phe Asp Ser Met Thr
            355                 360                 365
Arg Phe Asn Leu Ala Tyr Glu Phe Thr Thr Ile Ala Asp Ala Ser Gly
        370                 375                 380
Asn Ser Ile Tyr Gly Thr Asp Pro Asn Thr Ser Ser Leu Gln Gly Arg
385                 390                 395                 400
Ser Val Asn Glu Met Thr Ala Ala Tyr Tyr Gly Arg Thr Ala Asp Lys
                405                 410                 415
Phe Ala Pro Tyr
            420
```